United States Patent [19]
Barlozzari et al.

[11] Patent Number: 5,939,527
[45] Date of Patent: Aug. 17, 1999

[54] TETRAPEPTIDES AS ANTITUMOR AGENTS

[75] Inventors: Teresa Barlozzari, Wellesley; Andreas Haupt, Westborough; Bernd Janssen, Marlborough, all of Mass.; Christian Griesinger, Oberursel, Germany; Daniel Belik, Frankfurt, Germany; Michael Boretzky, Offenbach, Germany

[73] Assignee: BASF Aktiengesellschaft, Germany

[21] Appl. No.: 08/688,335

[22] Filed: Jul. 30, 1996

[51] Int. Cl.$^6$ ........................................................ C07K 5/00
[52] U.S. Cl. .............................................. 530/330; 514/18
[58] Field of Search ................................ 514/18; 530/330

[56] References Cited

U.S. PATENT DOCUMENTS

| | | | |
|---|---|---|---|
| 4,816,444 | 3/1989 | Pettit et al. | 514/17 |
| 5,502,032 | 3/1996 | Haupt et al. | 514/17 |
| 5,504,191 | 4/1996 | Pettit et al. | 530/330 |
| 5,530,097 | 6/1996 | Pettit et al. | 530/330 |
| 5,554,725 | 9/1996 | Pettit | 530/330 |
| 5,599,902 | 2/1997 | Pettit et al. | 530/330 |

FOREIGN PATENT DOCUMENTS

| | | |
|---|---|---|
| 0 398 558 | 11/1990 | European Pat. Off. |
| 0 598 129 | 5/1994 | European Pat. Off. |
| 9303054 | 2/1993 | WIPO |
| 93/23424 | 11/1993 | WIPO |

OTHER PUBLICATIONS

HCAPLUS, AN 1996: 457934, Pettit et al., WO 9614856, May 23, 1996, abstract.

HCAPLUS, AN 1996: 756324, Sakakibara et al., WO 9633212, Oct. 24, 1996, abstract.

Pettit, G. R., et al., "Antineoplastic Agents 337. Synthesis of Dolastatin–10 Structural Modifications," *Anti–Cancer Drug Design*, 10: 529–544 (1995).

Miyazaki, K., et al., "Synthesis and Antitumor Activity of Novel Dolastatin–10 Analogs," *Chem. Pharm. bull.*, 43 (10) : 1706–1718 (1995).

Pettit, G. R., et al., "The Isolation and Structure of a Remarkable Marine Animal Antineoplastic Constituent: Dolastatin 10", *J. Am. Chem. Soc.* 109: 6883–6885 (1987).

Bai, R., et al., "Structure–Activity Studies with Chiral Isomers and with Segments of the Antimitotic Marine Peptide Dolastatin 10", *Biochemical Pharmacology* 40 (8) : 1859–1864 (1990).

Pettit, G. R., et al., "Antineoplastic Agents. 220. Synthesis of Natural (–) —Dolastatin 15", *J. Am. Chem. Soc.*, 113: 6692–6693 (1991).

Pettit, G. R., et al., "Isolation and Structure of the Cytostatic Linear Depsipeptide Dolastatin 15", *J. Org. Chem.*, 54: 6005–6006 (1989).

Pettit, G.R. et al., "Isolation of Dolastatins 10–15 From the MarineMollusc *Dolabella Auricularia*," *Tetrahedron*, 49(41) : 9151–9170 (1993).

Pettit, G.R. et al., "The Dolastatins 20. A Convenient Synthetic Route to Dolastatin 15," *Tetrahedron*, 50 (42) : 12097–12108 (1994).

Bai, R., et al., "Dolastatin 15, a potent antimitotic depsipeptide derived from *Dolabella auricularia*. Interaction with tubulin and effects on cellular microtubules", 1–*Pharmacology* Abstract 117: 103735g P. 41 (1992).

Pettit, G. R., et al., "Isolation and Structure of the Cytostatic Depsipeptide Dolastatin 13 from the Sea Hare *Dolabella auricularia*", *J. Am. Chem. Soc.*, 111 (13) : 5015–5017 (1989).

*Primary Examiner*—Cecilia J. Tsang
*Assistant Examiner*—C. Delacroix-Muirheid
*Attorney, Agent, or Firm*—Hamilton, Brook, Smith & Reynolds, P.C.

[57] ABSTRACT

The present invention provides anti-tumor peptides of Formula I,

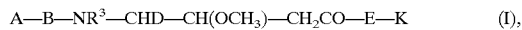

$$A-B-NR^3-CHD-CH(OCH_3)-CH_2CO-E-K \qquad (I),$$

and the acid salts thereof. A is an amino acid residue selected from the group consisting of N-methyl-D-prolyl, N-methyl-D-homoprolyl and N,N-dimethyl-2-ethylphenylglycyl, or an amino acid residue of the formula $R^1R^2N$—CHX—CO, wherein $R^1$ is a-methyl group or an ethyl group, $R^2$ is a hydrogen atom, a methyl group or an ethyl group, and X is an alkyl group. B is an amino acid residue selected from the group consisting of valyl, isoleucyl, leucyl, and 2-t-butylglycyl. $R^3$ is a hydrogen atom or a methyl group. D is a normal or branched $C_2$–$C_5$-alkyl group. E is an amino acid residue selected from the group consisting of prolyl, homoprolyl, 5-methylprolyl, and phenylalanyl, or E is a residue derived from an amino acid comprising a pyrrolidine group. K is an alkoxy group or an amino group.

An additional embodiment of the present invention is a method for treating a malignancy in a mammal, such as a human, comprising administering to the mammal an effective amount of a compound or compounds of Formula I in a pharmaceutically acceptable composition.

15 Claims, 1 Drawing Sheet

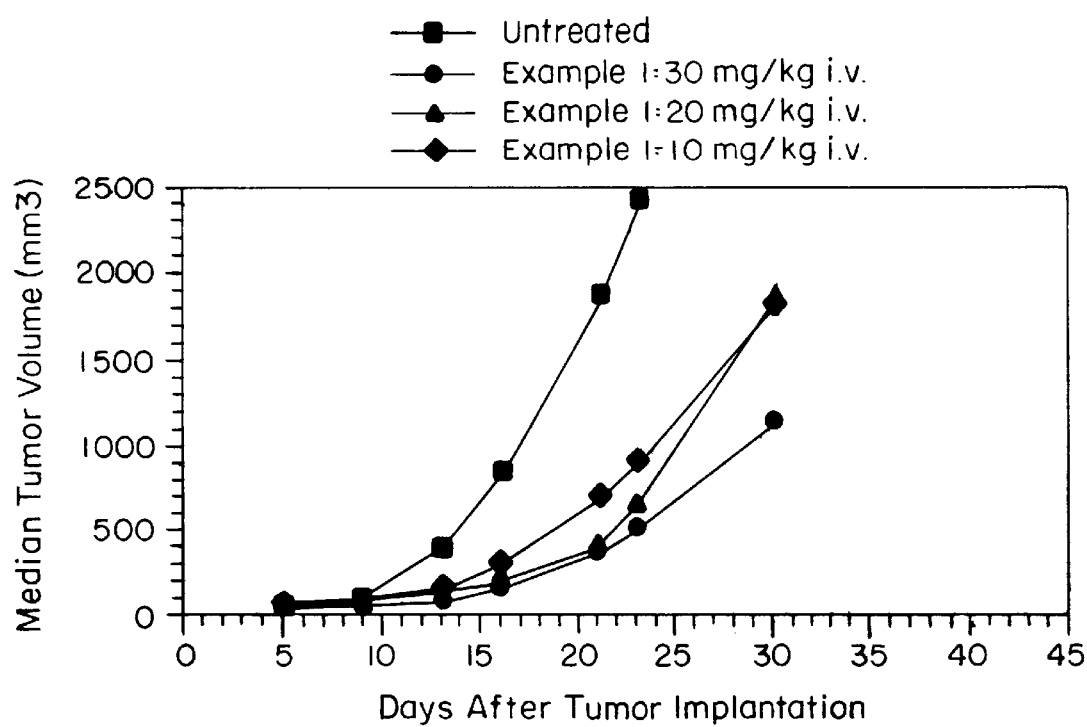
The Figure

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1:

Val Val Xaa Pro
1

(2) INFORMATION FOR SEQ ID NO:2:

(i) SEQUENCE CHARACTERISTICS:
        (A) LENGTH: 4 amino acids

```
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:2:

Val Val Xaa Xaa
1

(2) INFORMATION FOR SEQ ID NO:3:

(i) SEQUENCE CHARACTERISTICS:
        (A) LENGTH: 4 amino
acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:3:

Xaa Val Xaa Pro
1

(2) INFORMATION FOR SEQ ID NO:4:

(i) SEQUENCE CHARACTERISTICS:
        (A) LENGTH: 4 amino
acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

Pro Val Xaa Pro
1
```

TETRAPEPTIDES AS ANTITUMOR AGENTS

BACKGROUND OF THE INVENTION

A series of short peptides with significant activity as cell growth inhibitors have been isolated from the Indian Ocean sea hare *Dolabella auricularia* (Pettit et al., *J. Am. Chem. Soc.* 109: 6883–6885 (1987); Beckwith et al., *J. Natl. Cancer. Inst.* 85: 483–88 (1993); U.S. Pat. No. 4,816,444; European Patent Application Publication No. 398,558). These peptides are referred to as Dolastatins 1–15. Of these, Dolastatins 10 and 15 are the most potent cell growth inhibitors. Dolastatin 15, for example, inhibits the growth of the National Cancer Institute's P388 lymphocytic leukemia (PS system) cell line, a strong predictor of efficacy against various types of human malignancies. Dolastatin 10 and Dolastatin 15 effectively inhibit tubulin polymerization and growth of four different human lymphoma cell lines (Bai et al., *Biochem. Pharmacol.* 39: 1941–1949 (1990); Beckwith et al., supra (1993)).

The minute amounts of the Dolastatin peptides present in Dolabella auricularia (about 1 mg each per 100 kg sea hare) and the consequent difficulties in purifying amounts sufficient for evaluation and use, have motivated efforts toward the synthesis of the more promising of these compounds, including Dolastatin 10 (Pettit et al., *J. Am. Chem Soc.* 111: 5463–5465 (1989); Roux et al. *Tetrahedron* 50: 5345–5360 (1994); Shiori et al. *Tetrahedron* 49: 1913–1924 (1993)). Synthetic Dolastatin 10, however, suffers from disadvantages which include poor solubility in aqueous systems and the need for expensive starting materials for its synthesis. These disadvantages, in turn, have led to the synthesis and evaluation of structurally modified Dolastatin 10 derivatives (European Patent Application, Publication No. WO 93/03054; Japanese Patent Application No. 06,234,790; U.S. Pat. No. 5,502,032.

A need persists for synthetic compounds with the biological activity of Dolastatin 10 which have useful aqueous solubility and can be produced efficiently and economically.

SUMMARY OF THE INVENTION

The present invention provides anti-tumor peptides of Formula I,

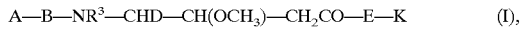

and the acid salts thereof. A is an amino acid residue selected from the group consisting of N-methyl-D-prolyl, N-methyl-D-homoprolyl and N,N-dimethyl-2-ethylphenylglycyl, or an amino acid residue of the formula $R^1R^2N-CHX-CO$, wherein $R^1$ is a methyl group or an ethyl group, $R^2$ is a hydrogen atom, a methyl group or an ethyl group, and X is a normal or branched $C_2-C_4$-alkyl group. B is an amino acid residue selected from the group consisting of valyl, isoleucyl, leucyl, and 2-t-butylglycyl. $R^3$ is a hydrogen atom or a methyl group. D is a normal or branched $C_2-C_5$-alkyl group. E is an amino acid residue selected from the group consisting of prolyl, homoprolyl, 5-methylprolyl, and phenylalanyl, or E is a residue derived from an amino acid comprising a pyrrolidine group. K is an alkoxy group, a benzyloxy group or a substituted amino group.

Another aspect of the present invention includes pharmaceutical compositions comprising a compound of Formula I and a pharmaceutically acceptable carrier.

An additional embodiment of the present invention is a method for treating a malignancy in a mammal, such as a human, comprising administering to the mammal an effective amount of a compound or compounds of Formula I in a pharmaceutically acceptable composition.

BRIEF DESCRIPTION OF THE DRAWING

The FIGURE is a graph showing tumor volume versus post-implantation time for four sets of mice; a control, or untreated, set; a set receiving a dose of compound 1 of 10 mg/kg; a set receiving a dose of compound 1 of 20 mg/kg and a set receiving a dose of compound 1 of 30 mg/kg.

DETAILED DESCRIPTION OF THE INVENTION

The present invention relates to peptides having antineoplastic activity. It also includes pharmaceutical compositions comprising these compounds and methods for treating cancer in a mammal, including a human, by administration of these compositions to the mammal.

Applicants have discovered that structural modification of Dolastatin 10 results in novel compounds with a surprisingly improved therapeutic potential for the treatment of neoplastic diseases, as compared to Dolastatin 10. Furthermore, the compounds of the present invention can be conveniently synthesized, as described below in detail.

Compounds of the present invention include anti-tumor peptides of Formula I:

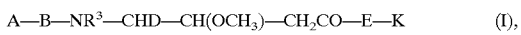

wherein

A is an amino acid residue selected from the group consisting of N-methyl-D-prolyl, N-methyl-D-homoprolyl and N,N-dimethyl-2-ethylphenylglycyl, or an amino acid residue of the formula $R^1R^2N-CHX-CO$;

$R^1$ is a methyl group or an ethyl group, $R^2$ is a hydrogen atom, a methyl group or an ethyl group;

X is a normal or branched $C_2-C_4$-alkyl group;

B is an amino acid residue selected from the group consisting of valyl, isoleucyl, leucyl, and 2-$^t$butylglycyl;

$R^3$ is a hydrogen atom or a methyl group;

D is a normal or branched $C_2-C_5$-alkyl group;

E is an amino acid residue selected from the group consisting of prolyl, homoprolyl, 5-methylprolyl, and phenylalanyl, or E is a residue derived from a carboxylic acid comprising a pyrrolidine group. E can be, for example:

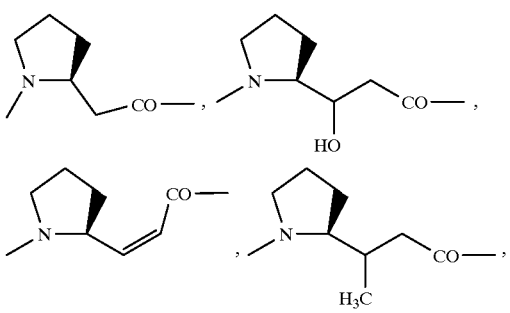

-continued

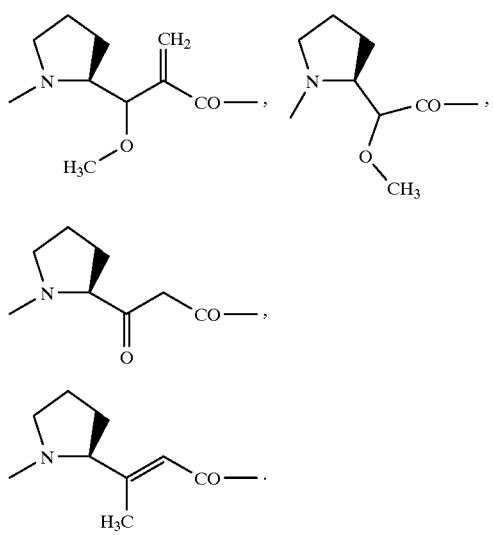

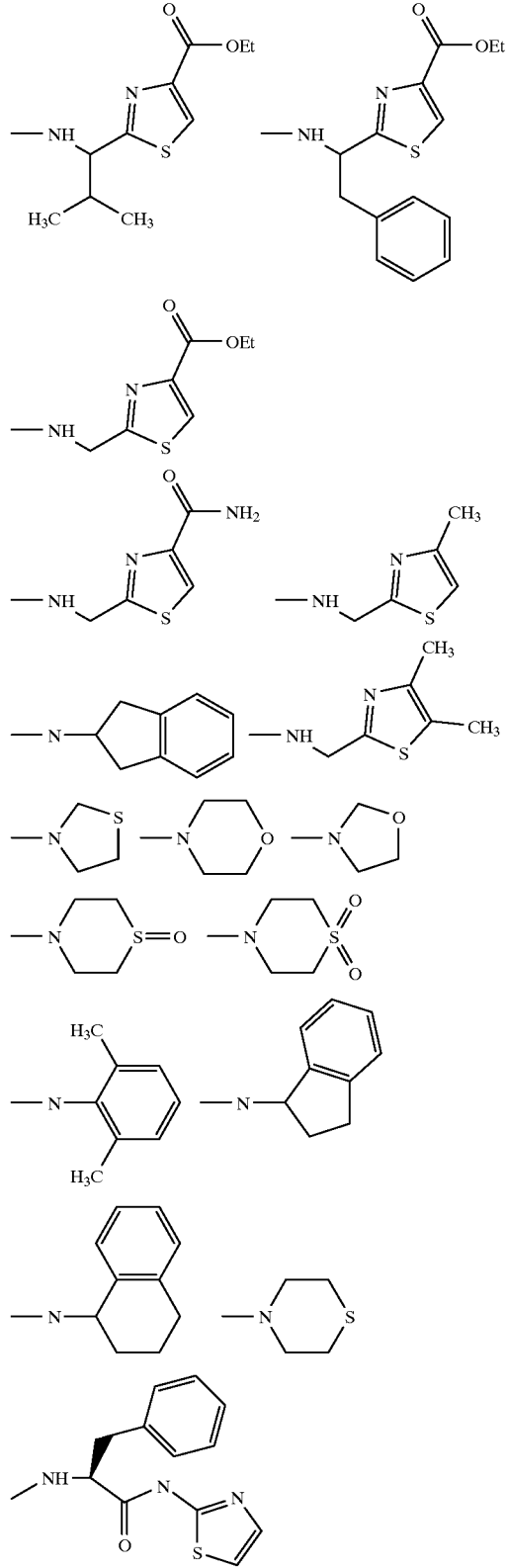

K can be a $C_1$–$C_4$-alkoxy group, a benzyloxy group or a substituted amino group. Examples of suitable amino groups include: —N($C_{1-3}$-alkyl)$C_{1-3}$-alkyl, —NH—$C_{1-8}$-alkyl, —NH—C(CH$_3$)$_2$CN, —NH—C(CH$_3$)$_2$CCH, —NH—C(CH$_3$)$_2$CH$_2$CH$_2$OH, —NH—C(CH$_3$)$_2$CH$_2$OH, —NH—$C_{3-8}$-cycloalkyl, —NH-[3,3,0]-bicyclooctyl, —NHCH(CH$_3$)CH(OH)C$_6$H$_5$, —N(CH$_3$)CH(CH$_3$)CH(OH)C$_6$H$_5$, —NH-quinolyl, —NH-pyrazyl, —NH—CH$_2$-benzimidazolyl, —NH-adamantyl, —NH—CH$_2$-adamantyl, —NH—CH(CH$_3$)-phenyl, —NH—C(CH$_3$)$_2$-phenyl, —N($C_{1-4}$-alkoxy)-$C_{1-4}$-alkyl, —N($C_{1-4}$-alkoxy)-CH$_2$-phenyl, —N($C_{1-4}$-alkoxy)phenyl, —N(CH$_3$)OCH$_2$-phenyl, —NH-(CH$_2$)$_v$-phenyl (v=0, 1, 2, or 3), which can be substituted by up to three substituents which can independently be CF$_3$, NO$_2$, methoxy, methyl, ethyl, N(CH$_3$)$_2$, halogen, or $C_{1-4}$-alkylsulfonyl, —NH-(CH$_2$)$_m$-naphthyl (m=0 or 1), —NH-(CH$_2$)$_2$-benzhydryl (w=0, 1, or 2), —NH-biphenyl, —NH-pyridyl, —NH—CH$_2$-pyridyl, —NH—CH$_2$—CH$_2$-pyridyl, —NH-benzothiazolyl, —NH-benzoisothiazolyl, —NH-benzopyrazolyl, —NH-benzoxazolyl, —NH-(CH$_2$)$_m$-fluorenyl (m=0 or 1), —NH-pyrimidyl, —NH-(CH$_2$)$_m$-indanyl (m=0 or 1), —NH-(CH$_2$CH$_2$O)$_y$—CH$_2$CH$_3$ (y=0, 1, 2, 3, 4, or 5), —NH-(CH$_2$CH$_2$O)$_y$—CH$_3$ (y=0, 1, 2, 3, 4, or 5), —NH—NH—C$_6$H$_5$, —NH—NCH$_3$—C$_6$H$_5$, —NH—NH—CH$_2$—C$_6$H$_5$, and —NH—NCH$_3$—CH$_2$—C$_6$H$_5$. K can also be selected from among the following:

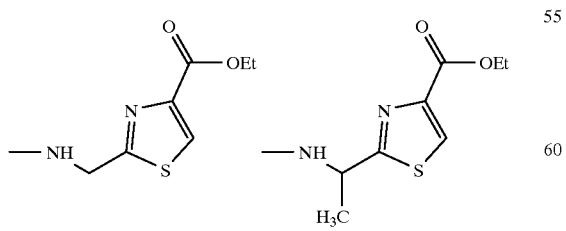

-continued
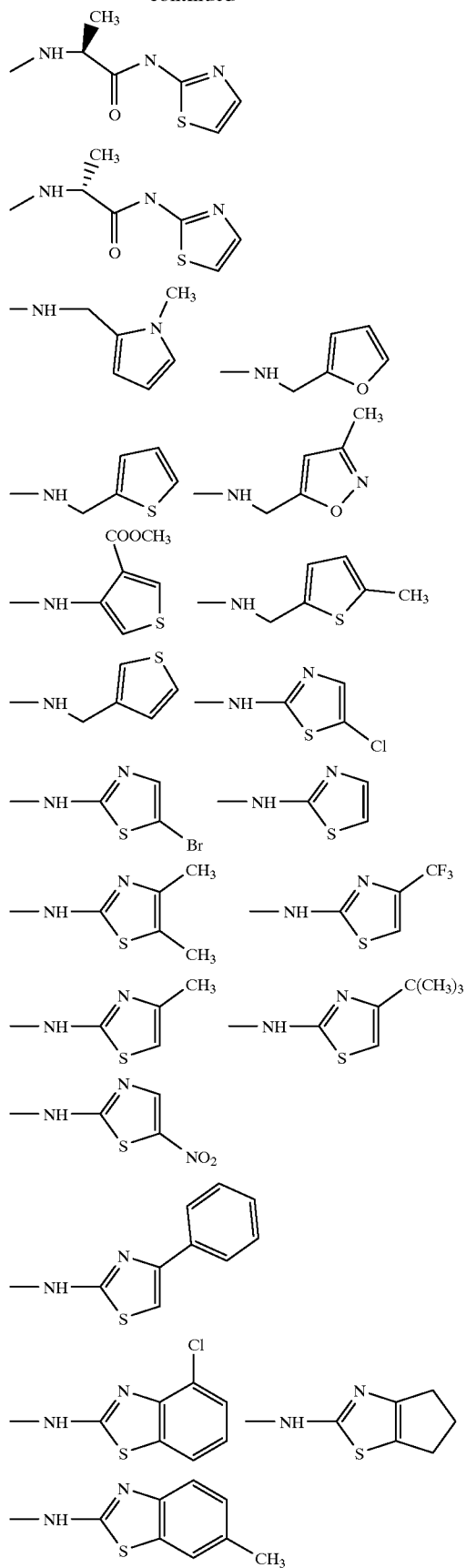
-continued
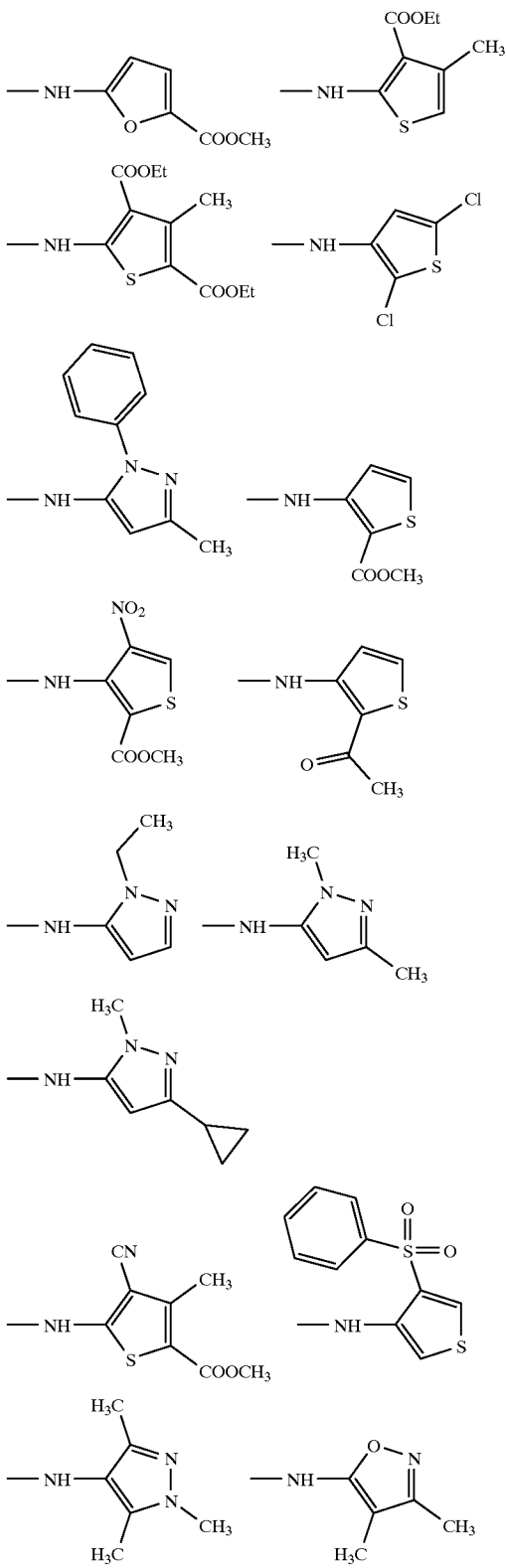

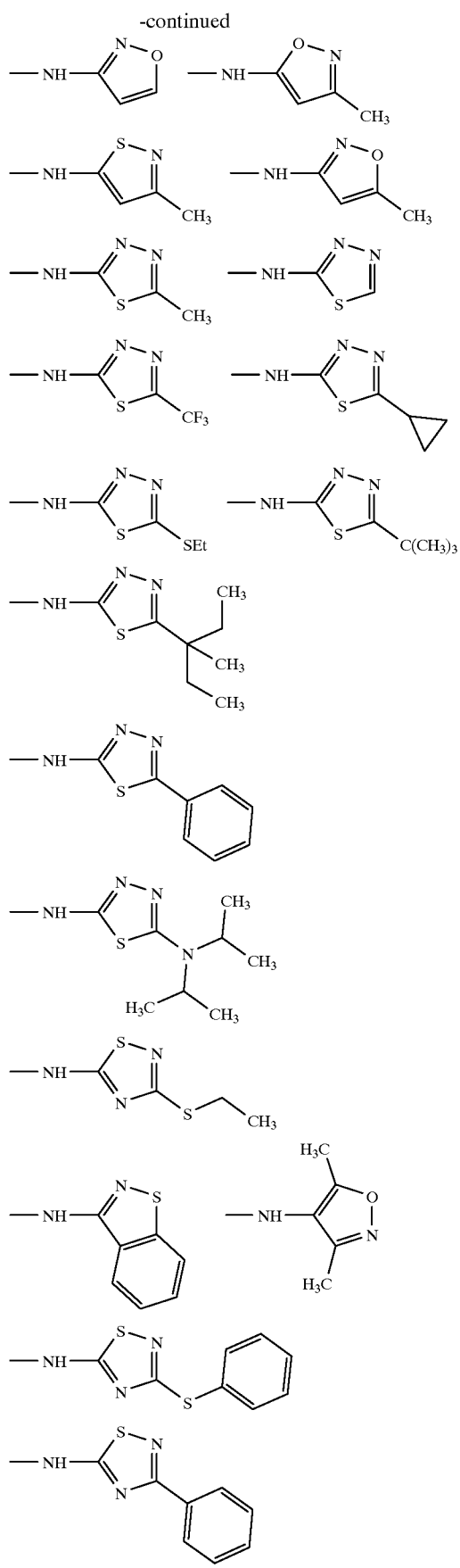
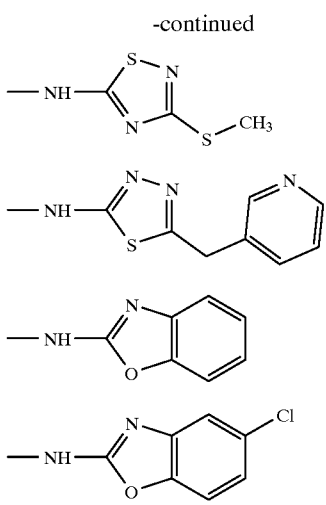

Preferred compounds of the present invention are of Formula I in which:

A is an amino acid residue selected from the group consisting of N-methyl-D-prolyl, N-methyl-D-homoprolyl and N,N-dimethyl-2-ethylphenylglycyl, or an amino acid residue of the formula $R^1R^2N$—CHX—CO, wherein $R^1$ is a methyl group, $R^2$ is a hydrogen atom or a methyl group, and X is an isopropyl, t-butyl or sec-butyl group;

B is an amino acid residue selected from the group consisting of valyl, isoleucyl and 2-$^t$butylglycyl;

$R^3$ is a methyl group;

D is an isopropyl, t-butyl or sec-butyl group;

E is a prolyl or homoprolyl residue, or a residue of a pyrrolidine-containing carboxylic acid selected from the group shown below:

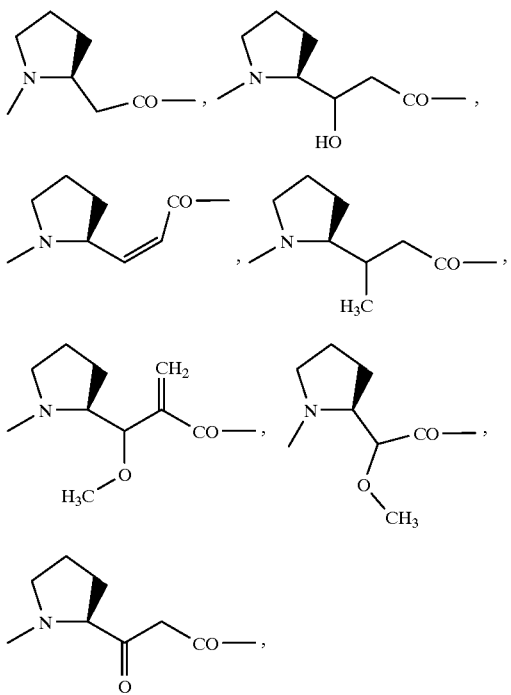

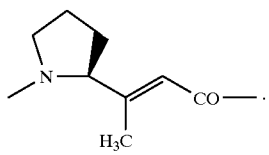

K is an alkoxy group selected from among —OCH₃, —OCH₂CH₃, and —OC(CH₃)₃ or an amino group selected from among the following: —NHCH₃, —NHCH₂CH₃, —NH(CH₂)₂CH₃, —NH(CH₂)₃CH₃, —NH(CH2)₄CH₃, —NH(CH₂)₅CH₃, —NH(CH2)₆CH₃, —NHCH(CH₃)₂ —NHCH(CH₂CH₃)₂,—NH (CH₂CH₂CH₃)₂, —NHC(CH₃)₃, —NH-cyclopropyl, —NH-cyclobutyl, —NH-cyclopentyl, —NH-cyclohexyl, —NH-cycloheptyl, —N[CH(CH₃)₂]CH(CH₃)₂, —N(CH₃)OCH₃, —N(CH₃) OCH₂CH₃, —N (CH₃) OCH₂CH₂CH₃, —N(CH₃) OCH (CH₃)₂, —N(CH₂CH₃) OCH₃, —N (CH₂CH₃) OCH₂CH₃, —N (CH₃) OCH₂C₆H₅, —N(OCH₃)CH₂—C₆H₅, —N(CH₃) OC₆H₅, —NH-phenyl, —NH-(3,4,5-trimethoxy)phenyl, —NH-(4-ethyl)phenyl, —NH—CH₂—C₆H₅, —NH(CH₂)₂C₆H₅, —NH(CH₂)₃C₆H₅, —NHCH (CH₃) CH (OH) C₆H₅, —N (CH₃) CH (CH₃) CH (OH) C₆H₅, —NH—CH₂-cyclohexyl, —NH-indanyl-(1), —NH—CH₂CF₃, —NHCH(CH₂F)₂, —NHC (CH₃)₂CH₂OH, —NH (CH₂CH₂O)₂CH₂CH₃, —NHC (CH₃)₂CN, —NH-quinolyl, —NH-pyrazyl, —NH-adamantyl(2), —NH-adamantyl(1), —NH—CH₂-naphthyl, —NH-benzhydryl, —NH-biphenyl, —NH-pyridyl, —NH—CH₂-pyridyl, —NH—CH₂—CH₂-pyridyl, —NH-benzothiazolyl, —NH-benzoiso-thiazolyl, —NH-benzopyrazolyl, —NH-benzoxazolyl, —NH-fluorenyl, —NH-pyrimidyl, —NH—CH₂—(4-methyl)-thiazolyl(2), —NH—CH₂-furanyl(2), —NH—CH₂-thienyl(2), —NH—CH₂—(5-methyl)thienyl(2), —NH-thiazolyl(2), —NH-isoxazolyl (3), —NH-(3-methyl)isoxazolyl(5), —NH-(3-methyl)isothiazolyl(5), —NH-(5-trifluoromethyl) thiadiazolyl (2), —NH-(5-cyclopropyl)thiadiazolyl(2), —NH-(4,5-dimethyl)thiazolyl(2), —NH-(5-methyl)thiadiazolyl(2), —Phe-thiazolyl(2)amide, —L—Ala-thiazolyl(2)amide, —D—Ala-thiazolyl(2)amide, or K is selected from among the heterocyclic amino groups shown below.

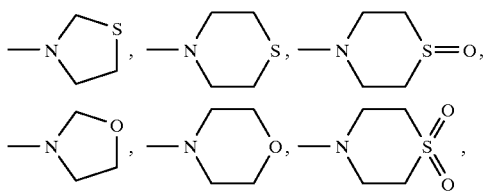

Synthetic Methods

The compounds of the present invention can be prepared by known methods of peptide synthesis. Thus, the peptides can be assembled sequentially from individual amino acids or by linking suitable small peptide fragments. In sequential assembly, the peptide chain is extended stepwise, starting at the C-terminus, by one amino acid per step. In fragment coupling, fragments of different lengths can be linked together, and the fragments in turn can be obtained by sequential assembly from amino acids or by fragment coupling of still shorter peptides.

In both sequential assembly and fragment coupling, it is necessary to link the units by forming an amide linkage, which can be accomplished via a variety of enzymatic and chemical methods. Chemical methods for forming the amide linkage are described in detail in standard references on peptide chemistry, including Muller, Methoden der organischen Chemie Vol. XV/2, 1–364, Thieme Verlag, Stuttgart, (1974); Stewart and Young, Solid Phase Peptide Synthesis, 31–34 and 71–82, Pierce Chemical Company, Rockford, Ill. (1984); Bodanszky et al., Peptide Synthesis, 85–128, John Wiley & Sons, New York, (1976). Preferred methods include the azide method, the symmetric and mixed anhydride method, the use of in situ generated or preformed active esters, the use of urethane protected N-carboxy anhydrides of amino acids and the formation of the amide linkage using coupling reagents, such as carboxylic acid activators, especially dicyclohexylcarbodiimide (DCC), diisopropylcarbodiimide (DIC), 1-ethoxycarbonyl-2-ethoxy-1,2-dihydroquinoline (EEDQ), 1-ethyl-3(3-dimethylaminopropyl)carbodiimide hydrochloride (EDCI), n-propane-phosphonic anhydride (PPA), N,N-bis (2-oxo-oxazolidinyl)imido-phosphoryl chloride (BOP-Cl), bromo-tris-pyrrolidinophosphonium hexafluorophosphate (PyBrop), diphenylphosphoryl azide (DPPA), Castro's reagent (BOP, PyBop), O-benzotriazolyl-N,N,N', N'-tetramethyluronium salts (HBTU), O-azabenzotriazolyl-N,N,N',N'-tetramethyluronium salts (HATU), diethylphosphoryl cyanide (DEPCN), 2,5-diphenyl-2,3-dihydro-3-oxo-4-hydroxythiophene dioxide (Steglich's reagent; HOTDO), and 1,1'-carbonyldiimidazole (CDI). The coupling reagents can be employed alone or in combination with additives such as N,N-dimethyl-4-aminopyridine (DMAP), N-hydroxybenzotriazole (HOBt), N-hydroxybenzotriazine (HOOBt), N-hydroxyazabenzotriazolyl (HOAt), N-hydroxysuccinimide (HOSu) or 2-hydroxypyridine.

Although the use of protecting groups is generally not necessary in enzymatic peptide synthesis, reversible protection of reactive groups not involved in formation of the amide linkage is necessary for both reactants in chemical synthesis. Three conventional protective group techniques are preferred for chemical peptide synthesis: the benzyloxycarbonyl (Z), the t-butoxycarbonyl (Boc) and the 9-fluorenylmethoxycarbonyl (Fmoc) techniques. Identified in each case is the protective group on the a-amino group of the chain-extending unit. A detailed review of amino-acid protective groups is given by Müller, Methoden der organischen Chemie Vol. XV/1, pp 20–906, Thieme Verlag, Stuttgart (1974). The units employed for assembling the peptide chain can be reacted in solution, in suspension or by a method similar to that described by Merrifield, J. Amer. Chem. Soc. 85: 2149 (1963). Particularly preferred methods are those in which peptides are assembled sequentially or by fragment coupling using the Z, Boc or Fmoc protective group technique.

Solvents suitable for peptide synthesis include any solvent which is inert under the reaction conditions, especially water, N,N-dimethylformamide (DMF), dimethyl sulfoxide (DMSO), acetonitrile, dichloromethane (DCM), 1,4-dioxane, tetrahydrofuran (THF), N-methyl-2-pyrrolidone (NMP), ethyl acetate and mixtures of these solvents.

For coupling of the amino acid following the the N-methylated γamino acid derivative, the use of either BOC-protected amino acid N-carboxy anhydrides (NCAs), Z-protected NCAs or the use of pivaloyl chloride or HATU as the condensing agent is most advantageous for this type of coupling.

Peptides which are dialkylated at the amino terminus can be prepared using the appropriate N,N-dialkylamino acid as a building block or by hydrogenating N-unsubstituted peptides in solution in the presence of an appropriate aldehyde or ketone and a catalyst such as palladium on charcoal.

The various non-naturally occurring amino acids disclosed herein can be obtained from commercial sources or synthesized from commercially available materials using methods known in the art. For example, the moiety —NR$^3$—CHD—CH(OCH$_3$)CH$_2$CO— can be prepared according to published procedures (Shiori et al. in *Peptide Chemistry*, Yanaihara, ed. (1989); Pettit et al., *J. Am. Chem. Soc.* 111: 5463 (1989); Shiori et al., *Tet. Lett.:* 931–934 (1991); Koga et al., *Tet. Lett.:* 2395–2398 (1991)).

Methods of Use of the Claimed Compounds

In another embodiment, the present invention comprises a method for partially or totally inhibiting formation of, or otherwise treating (e.g., reversing or inhibiting the further development of) solid tumors (e.g., tumors of the lung, breast, colon, prostate, bladder, rectum, or endometrial tumors) or hematological malignancies (e.g., leukemias, lymphomas) in a mammal, for example, a human, by administering to the mammal a therapeutically effective amount of a compound or a combination of compounds of Formula I. The compound(s) of Formula I can be administered alone or in conjunction with other drugs, such as other anti-cancer drugs or in a pharmaceutical composition further comprising an acceptable carrier or diluent, and, optionally, other drugs. Administration can be by any means which are conventional for pharmaceutical, preferably oncological, agents, including oral and parenteral means such as subcutaneously, intravenously, intramuscularly and intraperitoneally, nasally or rectally.

The dosage to be administered to the mammal, such as a human, is a therapeutically effective amount of a compound described herein. The therapeutically effective amount can be administered in a single dose or multiple doses in a given period of time (e.g., a single daily dose or two or more doses a day). As used herein, "therapeutically effective amount" is an amount sufficient to inhibit (partially or totally) formation of a tumor or a hematological malignancy or to reverse development of a solid tumor or other malignancy or prevent or reduce its further progression. For a particular condition or method of treatment, the dosage is determined empirically, using known methods, and will depend upon factors such as the biological activity of the particular compound employed; the means of administration; the age, health and body weight of the recipient; the nature and extent of the symptoms; the frequency of treatment; the administration of other therapies; and the effect desired. A typical daily dose will be from about 0.5 to about 50 milligrams per kilogram of body weight by oral administration and from about 0.05 to about 20 milligrams per kilogram of body weight by parenteral administration.

The compounds of the present invention can be administered in conventional solid or liquid pharmaceutical administration forms, for example, uncoated or (film-) coated tablets, capsules, powders, granules, suppositories or solutions. These are produced in a conventional manner. The active substances can, for this purpose, be processed with conventional pharmaceutical aids such as tablet binders, fillers, preservatives, tablet disintegrants, flow regulators, plasticizers, wetting agents, dispersants, emulsifiers, solvents, sustained release compositions, antioxidants and/or propellant gases (cf. H. Sücker et al.: Pharmazeutische Technologie, Thieme-Verlag, Stuttgart, 1978). The administration forms obtained in this way typically contain from about 1 to about 90% by weight of the active substance.

The following examples are intended to illustrate the invention but are not to be considered limitations of the invention.

EXAMPLES

The proteinogenous amino acids are abbreviated in the examples using the known three-letter code. Other abbreviations employed are: TFA=trifluoroacetic acid; Ac=acetic acid; DCM=dichloromethane; DMSO=dimethylsulfoxide; Bu=butyl; Et=ethyl; Me=methyl; Bzl=benzyl; LDA=lithium diisopropylamide; LHMDS=lithium hexamethyldisilazide; HMPA=hexamethylphosphoric triamide.

General Materials and Methods

The compounds of the present invention are synthesized by classical solution synthesis using standard Z- and Boc-methodology as discussed above.

Purification was carried out by crystallization from the appropriate solvents or mixtures thereof, by medium pressure chromatography (stationary phase: HD-SIL C-8, 20–45 micron, 100 Angstrom; mobile phase: gradient with A=0.1% TFA/water, B=0.1% TFA/MeOH), or by preparative HPLC (stationary phase: Waters Delta-Pak C-18, 15 micron, 100 Angstrom; mobile phase: gradient with A=0.1% TFA/water, B=0.1% TFA/MeOH or 0.1% TFA/Acetonitril). The purity of the resulting products was determined by analytical HPLC (stationary phase: 100 2.1 mm VYDAC C-18, 300 Angstrom; mobile phase: acetonitrile-water gradient, buffered with 0.1% TFA, 40% C). Characterization was by mass spectroscopy (ESI or FAB-MS).

Example 1

Synthesis of (3R,4S)-4[N(N,N-dimethyl-L-valyl-L-valvl)-N-methylamino)-3-methoxy-5-methyl-hexanoyl-prolylthiazolvl(2)-amide (Compound 1)

Synthesis of t-butyl-(4S)-4-(N-benzyloxycarbonylamino)-5-methyl-3-oxohexanoate

To an ice-cooled solution of Z-valine (5 g, 19.9 mmol) in 60 ml tetrahydrofurane was added N,N'-cabonyldiimidazole (3.55 g, 22.3 mmol) in one portion and stirred for 3 h. At −78° C., tert-butyl acetate (13.5 ml, 100 mmol) was dropped to a solution of LDA (90 mmol) in tetrahydrofurane (270 ml). After 30', the imidazolide solution was added dropwise via double-ended needle to the enolate. The resulting mixture was stirred for 2 h until the temperature rose to −15° C. The reaction was quenched with 400 ml saturated aqueous NH$_4$Cl and extracted with ether (3×200 ml). The combined organic extracts were washed with 2N aqueous HCl (50 ml), saturated aqueous NaHCO$_3$ (2×50 ml), dried over magnesium sulfate and evaporated to dryness in vacuo. The residue was purified by column chromatography on silica gel using ethyl acetate-hexane (1:4) as an eluent to give the product as a colorless oil (6.88 g)

MS: calc. monoisotopic mass 349.19; found ESI-: 348.1

Synthesis of t-butyl-(3R,4S)-4-(N-benzyloxy-carbonylamino)-3-hydroxy-5-methyl-hexanoate To a solution of t-butyl-(4S)-4-(Nbenzyloxycarbonyl-amino)-5-methyl-3-oxohexanoate (6.0 g, 17.1 mmol) in 70 ml ethanol at 0° C. was added potassium borohydride (3.23 g, 58.8 mmol). After stirring for 4 h at 0° C. and 12 h at room temperature, the reaction mixture was acidified with glacial acetic acid to pH 4 and concentrated in vacuo. The residue was dissolved in a mixture of 200 ml ethyl acetate and 200 ml water. After additional washings of the aqueous phase with ethyl acetate (3×50 ml), the combined organic extracts were dried over magnesium sulfate and concentrated in vacuo. The crude product was purified by column chromatography on silica gel using ethyl acetate-hexane (1:4) as an eluent to give the alcohol as a white solid (5.31 g).

MS: calc. monoisotopic mass: 351.2; found ESI+: 352.2

Synthesis of t-butyl-(3R,4S)-4-(N-benzyloxycarbonyl-N-methyl-amino)-3-methoxy-5-methyl-hexanoate A solution of t-butyl-(3R,4S)-4-(N-benzyloxycarbonyl-amino)-3-hydroxy-5-methyl-hexanoate (3.027 g, 8.624 mmol) in tetrahydrofurane (40 ml) was added to a solution of LHMDS (24.0 mmol) in HMPA (4.5 ml, 25.7 mmol) and tetrahydrofurane (40 ml) at −78° C. After stirring for 20', methyltriflate (5.68 ml, 51.7 mmol) was added. After 1 h, the reaction was stopped by adding 70 ml aqueous 10% citric acid. The mixture was extracted with ethyl acetate (3 x). The combined organic extracts were washed with saturated aqueous NaHCO$_3$ (100 ml), dried over magnesium sulfate and concentrated in vacuo. The crude product was purified by column chromatography on silica gel, using ethyl acetate-hexane (1:4) as an eluent to give the desired product as a colorless oil (2.456 g).

MS: calc. monoisotop. mass 379.24; found FAB-MS [M+H]$^+$: 380

Synthesis of t-butyl-(3R,4S)-4-(N-methylamino)-3-methoxy-5-methyl- hexanoate To a solution of t-butyl-(3R,4S)-4-(N-benzyloxycarbonyl-N-methylamino)-3-methoxy-5-methyl-hexanoate (3.855 g, 10.17 mmol) in 100 ml methanol was added 10% Pd/C (0.541 g) and the mixture was hydrogenated until completion of the deprotection (tlc control). The catalyst was removed by filtration and the filtrate concentrated in vacuo. The resulting amorphous solid (2.49 g) can be crystallized from ether by adding a solution of HCl in dioxane.

MS: calc. monoisotopic mass 245.2; found FAB-MS [M+H]$^+$246

Synthesis of t-butyl-(3R,4S)-4-EN-(benzyloxycarbonylL-valyl)-N-methylaminol-3-methoxy-5-methyl-hexanoate To a solution of Z-valine (3.672 g, 14.6 mmol) and pivaloylchloride (1.8 ml, 14.6 mmol) was added diisopropylethylamine (2.5 ml, 14.6 mmol) at −15° C. After 1 h, t-butyl-(3R,4S)-4-(N-methylamino)-3-methoxy-5-methyl hexanoate (1.79 g, 7.3 mmol) and diisopropylethylamine (1.25 ml, 7.3 mmol) were added. The resulting mixture was stirred for 3 h at 0° C., 20 h at room temperature and then concentrated in vacuo. The reaction mixture was dissolved in ethyl acetate (100 ml), washed with 10% aqueous citric acid (2×30 ml), sat. aqueous NaHCO$_3$ (30 ml), dried over magnesium sulfate and concentrated in vacuo. The crude product was purified by column chromatography on silica gel using ethyl acetate-hexane (1:4) as eluent to give the dipeptide as a colorless oil (1.804 g).

MS: calc. monoisotopic mass 478.3; found FAB-MS [M+H]$^+$479

Synthesis of t-butyl-(3R,4S)-4-[N-(L-valyl)N-methylamino]-3-methoxy-5-methyl-hexanoate To a solution of t-butyl-(3R,4S)-4-[N-(benzyloxycarbonyl-L-valyl)-N-methylamino]-3-methoxy-5-methyl hexanoate (1.804 g, 3.77 mmol) in methanol (60 ml) was added 10% Pd/C (0.26 g) and the mixture was hydrogenated until completion (tlc control). The catalyst was removed by filtration and the filtrate was concentrated in vacuo to give the deprotected dipeptide unit (1.27 g).

MS: calc. monoisotopic mass 344.27; found FAB-MS [M+H]$^+$345

Synthesis of t-butyl-(3R,4S)-4-[N-(N,N-dimethyl-L-valyl-Lvalyl)-N-methylamino]-3-methoxy-5-methyl-hexanoate t-Butyl-(3R,4S)-4-[N-(L-valyl)-N-methylamino]-3methoxy-5-methyl hexanoate (0.357 g, 1.038 mmol) and N,N-dimethylvaline (0.301 g, 2.076 mmol) were dissolved in 3 ml DMF and cooled to 0° C. DEPC (0.496 ml, 2.283 mmol) was added, followed by diisopropylethylamine (0.391 ml, 2.283 mmol). After stirring at 0° C. for 3 h and at room temperature for 16 h, the reaction mixture was diluted with saturated aqueous NaHCO$_3$ (20 ml), washed with toluene/ethylacetate 2:1 (3x). The combined organic layers were extracted with 2N aqueous HCl (3×10 ml). The aqueous phase was then neutralized with NaHCO$_3$ and extracted with toluene/ethyl acetate (2:1) (3×20 ml). The organic layer was dried over magnesium sulfate and concentrated in vacuo. The crude product was purified by crystallization from ether by adding a solution of HCl in dioxane to give the tripeptide as a white solid (0.433 g).

MS: calc. monoisotopic mass 471.37; found FAB-MS [M+H]$^+$472

Synthesis of (3R,4S)-4-[N-(N,N-dimethyl-L-valyl-L-valyl)N-methylamino]-3-mothoxy-5-methyl-hexanoic acid To a solution of t-butyl-(3R,4S)-4-[N-(N,N-dimethyl-L-valyl-L-valyl)-N-methylamino)-3-methoxy-5-methylhexanoate (0.22 g, 0.433 mmol) in dichloromethane (2 ml) was added trifluoroacetic acid (2 ml). After stirring for 2 h, the reaction mixture was concentrated in vacuo. Reevaporation of the residue with toluene (5×10 ml) gave the deprotected product (0.268 g) which was used for the next step without further purification.

MS: calc. monoisotopic mass 415.3; found FAB-MS [M+H]$^+$416

Synthesis of (2S)-N-(t-butyloxycarbonyl)-prolylthiazolyl(2)-amide

To a precooled solution of 0.215 g Boc-Proline (1 mmol) and 0.1 g 2-aminothiazole (1 mmol) in 2 ml DMF were added 0.6 ml N-ethylmorpholine, followed by 0.88 g PPA (50% solution in ethyl acetate). The mixture was stirred at 0° C. for 1 h and at room temperature for 24 h. The solvents were evaporated under reduced pressure and the residue diluted with ethyl acetate, washed with 1M aqu. potassium hydrogen sulfate, saturated aqueous sodium hydrogen carbonate, water, dried over magnesium sulfate and concentrated in vacuo. The residue was recrystallized from ethyl acetate-hexane to give the desired product as a white solid (0.235 g).

ESIMS: 298.1 (+1); calc. 297.11

Synthesis of prolyl-thiazolyl(2)-amide

To a solution of (2S)-N-(t-butylaxycarbonyl)-prolylthiazolyl(2)-amide (0.131 g, 0.44 mmol) in dichloromethane (2 ml) was added trifluoroacetic acid (2 ml). After stirring for 2 h, the reaction mixture was concentrated in vacuo. Reevaporation of the residue with toluene (5×10 ml) gave the deprotected product which was used in the next step without further purification.

Synthesis of (3R,4S)-4-[N-(N,N-dimethyl-L-valyl-L-valyl)-N-methylamino]-3-methoxy-5-methyl-hexanoyl prolyl-thiazolyl(2)-amide (Compound 1)

To a precooled solution of 0.268 g (3R,4S)-4-[N(N,N-dimethyl-L-valyl-L-valyl)-N-methylamino)-3-methoxy-5-methyl-hexanoic acid (0.44 mmol) and prolylthiazolyl(2)-amide (0.44 mmol) in 10 ml DMF were added 0.1 ml DEPC (0.46 mmol) and 1.32 mmol triethylamine. After stirring at 0° C. for 3 h and at room temperature for 16 h, the reaction mixture was diluted with saturated aqueous NaHCO$_3$ (20 ml) and washed with toluene/ethylacetate 2:1 (3 x). The organic layers were extracted with 2N aqu. HCl (3×10 ml). The combined aqueous layers were adjusted to pH 8.5 with NaHCO$_3$ and extracted with toluene/ethyl acetate (2:1) (3×20 ml). The combined organic extracts were dried over magnesium sulfate and concentrated in vacuo to yield 0.198 g (0.33 mmol) of the desired product. The compound was further characterized by fast atom bombardment mass spectrometry ([M+H]$^+$=595.4).

The following table lists additional compounds that have been prepared via a similar route and the molecular weight determined for each by mass spectroscopy. These compounds correspond to the indicated sequences:
Compounds 1–6, 9–22 and 42–44: SEQ ID NO.: 1;
Compounds 7, 8, 30, 36–41 and 45: SEQ ID NO.: 2;
Compounds 23, 25, 27–29, 31,32 and 35: SEQ ID NO.: 3;
Compounds 24, 26, 33 and 34: SEQ ID NO.: 4.

TABLE I

| Compound | Compound Sequence | | | | Molecular weight |
|---|---|---|---|---|---|
| 2 | Xaa | Val | Xae | Xan | 588 |
| 3 | Xaa | Val | Xae | Xag | 526 |
| 4 | Xaa | Val | Xae | Xar | 602 |
| 5 | Xaa | Val | Xae | Xax | 660 |
| 6 | Xaa | Val | Xae | Xaw | |
| 7 | Xaa | Val | Xae | Xba | 616 |
| 8 | Xaa | Val | Xae | Xbb | 660 |
| 9 | Xaa | Val | Xae | Xak | 645 |
| 10 | Xaa | Val | Xae | Xap | 678 |
| 11 | Xaa | Val | Xae | Xas | 616 |
| 12 | Xaa | Val | Xae | Xat | 616 |
| 13 | Xaa | Val | Xae | Xah | 554 |
| 14 | Xaa | Val | Xae | Xao | 616 |
| 15 | Xaa | Val | Xae | Xay | 596 |
| 16 | Xaa | Val | Xae | Xau | 616 |
| 17 | Xaa | Val | Xaf | Xau | 630 |
| 18 | Xaa | Val | Xaf | Xam | 624 |
| 19 | Xaa | Val | Xaf | Xav | 631 |
| 20 | Xaa | Val | Xaf | Xal | 637 |
| 21 | Xaa | Val | Xae | Xaz | 527 |
| 22 | Xaa | Val | Xae | Xav | 602 |
| 23 | Xac | Val | Xae | Xaz | 525 |
| 24 | Xab | Val | Xae | Xai | 579 |
| 25 | Xac | Val | Xae | Xai | 593 |
| 26 | Xab | Val | Xae | Xav | 601 |
| 27 | Xad | Val | Xae | Xav | 679 |
| 28 | Xac | Val | Xae | Xav | 615 |
| 29 | Xad | Val | Xae | Xaz | 589 |
| 30 | Xaa | Val | Xae | Xbl | 689 |
| 31 | Xad | Val | Xae | Xaq | 651 |
| 32 | Xad | Val | Xae | Xai | 657 |
| 33 | Xab | Val | Xae | Xaz | 511 |
| 34 | Xab | Val | Xae | Xaq | 573 |
| 35 | Xac | Val | Xae | Xaq | 587 |
| 36 | Xaa | Val | Xae | Xbc | 569 |
| 37 | Xaa | Val | Xae | Xbd | 583 |
| 38 | Xaa | Val | Xae | Xbe | 571 |
| 39 | Xaa | Val | Xae | Xbf | 553 |
| 40 | Xaa | Val | Xae | Xbg | 581 |
| 41 | Xaa | Val | Xae | Xbh | 645 |
| 42 | Xaa | Val | Xae | Pro | Xbh | 742 |
| 43 | Xaa | Val | Xae | Pro | Xbi | 666 |
| 44 | Xaa | Val | Xae | Pro | Xbk | 666 |
| 45 | Xaa | Val | Xae | Xbm | 675 |

The symbols X__ in Table I have the following meanings:
Xaa: N,N-Dimethylvaline
Xab: N-Methyl-D-proline
Xac: N-Methyl-D-homoproline Xad:

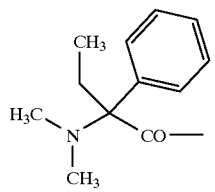

Xae:

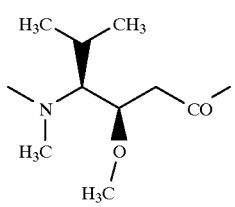

Xaf:

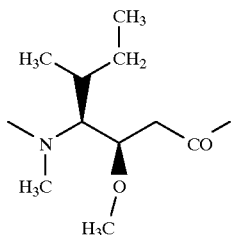

Xag:

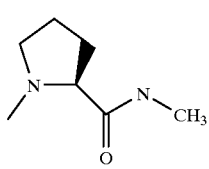

Xah:

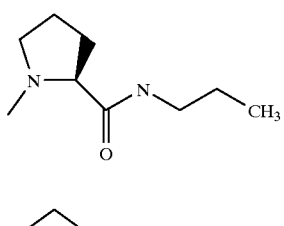

Xai:

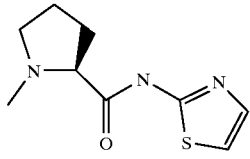

Xak:

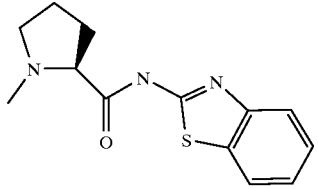

Xal:

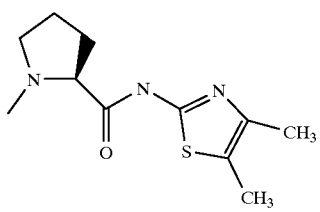

Xam:
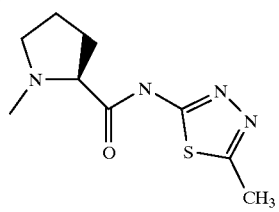
Xan:
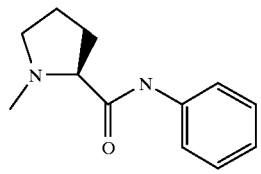
Xao:
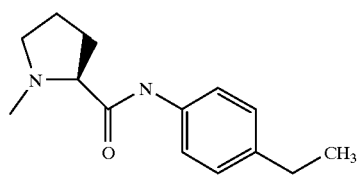
Xap:
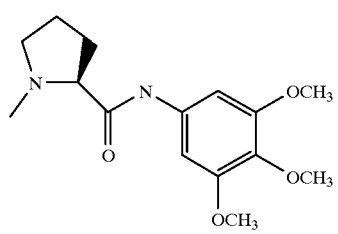
Xaq:
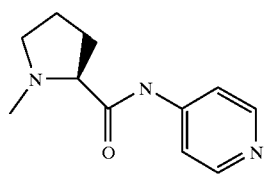
Xar:
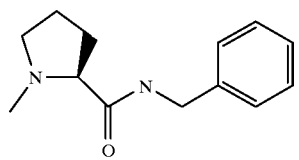
Xas:
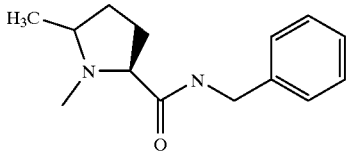
Xat:
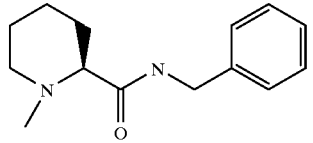
Xau:
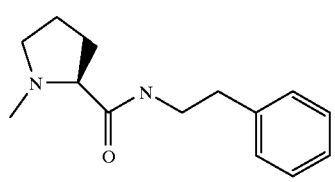
Xav:
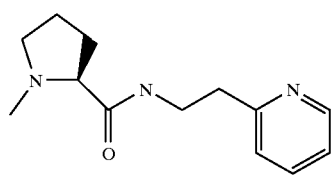
Xaw:
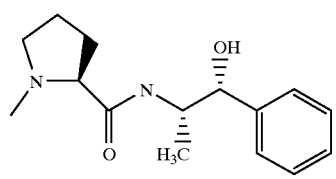
Xax:
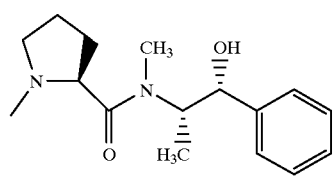
Xay:
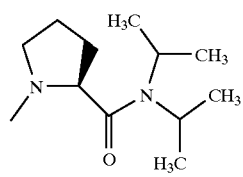
Xaz:
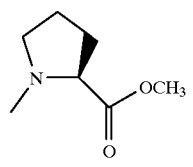
Xba:
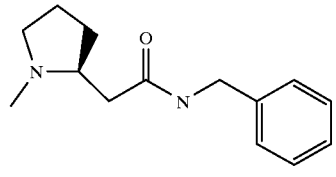
Xbb:
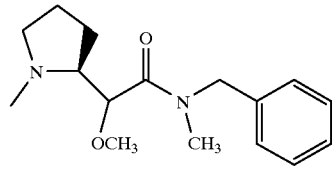

Xbc: 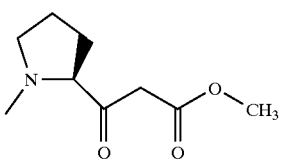

Xbd: 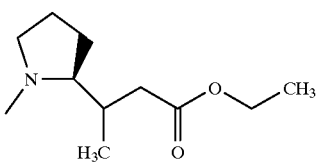

Xbe: 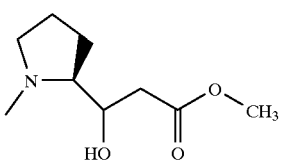

Xbf: 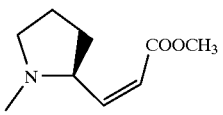

Xbg: 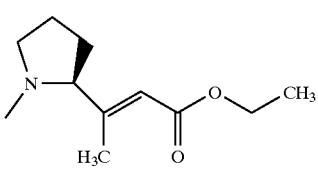

Xbh: 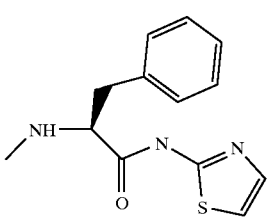

Xbi: 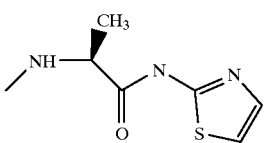

Xbk: 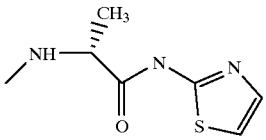

Xbl: 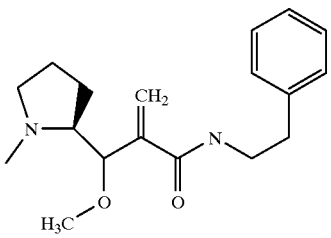

Xbm: 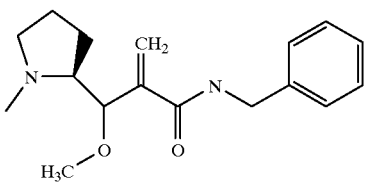

Example 2

Determination of In Vitro Cytotoxicity

Cytotoxicity was measured using the microculture tetrazolium assay (MTT), a standard methodology for adherent cell lines. Details of this assay have been published (Alley, et al., *Cancer Research* 48: 589–601 (1988)). Exponentially growing cultures of HT-29 colon carcinoma cells were used to make microtiter plate cultures. Cells were seeded at 5000–20,000 cells per well in 96-well plates (in 150 μl of media), and grown overnight at 37° C. Test compounds were added in 10-fold dilutions varying from $10^{-4}$M to $10^{-10}$M. Cells were then incubated for 48 hours. To determine the number of viable cells in each well, the MTT dye was added (50 μl of 3 mg/ml solution of 3-(4,5-dimethylthiazol-2-yl)-2,5-diphenyltetrazolium bromide in saline). This mixture was incubated at 37° C. for 5 hours, and then 50 μl of 25% SDS, pH 2, was added to each well. After an overnight incubation, the absorbance of each well at 550 nm was read using an ELISA reader. The values for the mean +/− SD of data from replicated wells were calculated, using the formula % T/C (% viable cells treated/control).

$$\frac{\text{OD of treated cells}}{\text{OD of control cells}} \times 100 = \% \ T/C$$

The concentration of test compound which gives a T/C of 50% growth inhibition was designated as the $IC_{50}$ value.

The results of the in vitro evaluation of compounds is presented in Table II.

TABLE II

| COMPOUND | $IC_{50}$ [M] |
| --- | --- |
| 1 | $6 \times 10^{-8}$ |
| 2 | $1 \times 10^{-7}$ |
| 3 | $7 \times 10^{-7}$ |
| 4 | $5 \times 10^{-7}$ |
| 5 | $2 \times 10^{-7}$ |
| 7 | $2 \times 10^{-6}$ |
| 8 | $4 \times 10^{-7}$ |
| 9 | $3 \times 10^{-8}$ |
| 10 | $3 \times 10^{-8}$ |
| 11 | $9 \times 10^{-7}$ |

TABLE II-continued

| COMPOUND | IC$_{50}$ [M] |
|---|---|
| 12 | $1 \times 10^{-6}$ |
| 13 | $3 \times 10^{-7}$ |
| 14 | $3 \times 10^{-8}$ |
| 15 | $8 \times 10^{-7}$ |
| 17 | $2 \times 10^{-7}$ |
| 18 | $2 \times 10^{-8}$ |
| 19 | $2 \times 10^{-7}$ |
| 20 | $5 \times 10^{-8}$ |
| 21 | $9 \times 10^{-9}$ |
| 22 | $9 \times 10^{-8}$ |
| 23 | $3 \times 10^{-8}$ |
| 24 | $9 \times 10^{-8}$ |
| 25 | $1 \times 10^{-7}$ |
| 26 | $6 \times 10^{-7}$ |
| 27 | $2 \times 10^{-7}$ |
| 28 | $3 \times 10^{-7}$ |
| 29 | $9 \times 10^{-9}$ |
| 30 | $8 \times 10^{-10}$ |
| 31 | $3 \times 10^{-8}$ |
| 32 | $1 \times 10^{-7}$ |
| 33 | $1 \times 10^{-7}$ |
| 34 | $3 \times 10^{-7}$ |
| 35 | $3 \times 10^{-7}$ |
| 36 | $3 \times 10^{-8}$ |
| 38 | $3 \times 10^{-8}$ |
| 39 | $2 \times 10^{-7}$ |
| 41 | $3 \times 10^{-7}$ |
| 42 | $9 \times 10^{-9}$ |
| 43 | $4 \times 10^{-8}$ |
| 44 | $5 \times 10^{-7}$ |
| 45 | $6 \times 10^{-9}$ |

Example 3

Determination of In Vivo Activity

Compounds of this invention were further tested in preclinical assays for in vivo activity which is indicative of clinical utility. Such assays were conducted with nude mice into which tumor tissue, preferably of human origin, had been transplanted (xenografted), as is well known in this field. Test compounds were evaluated for anti-tumor efficacy following administration to the xenograft-bearing mice.

Human breast tumors (MX-1) which had been grown in athymic nude mice were transplanted into new recipient mice, using tumor fragments which were about 50 mg in size. The day of transplantation was designated as day 0. The mice were divided into four groups of 5–10 mice each. An untreated group served as the control. Three groups were treated by subcutaneous injection of compound 1, with each group receiving three doses per week of 30, 20 or 10 mg/kg body weight. Doses were administered on days 5, 7, 9, 12, 14, 16, 19, 21 and 23 post post-implantation.

Tumor diameters and body weights were measured twice weekly. Tumor volumes were calculated using the diameters measured with Vernier calipers, and the formula $$(length \times width^2)/2 = mm^3 \text{ of tumor volume}$$

Mean tumor volumes are calculated for each treatment group, and T/C values determined for each group relative to the untreated control tumors.

Results

The results of in vivo evaluation of compound 1 are presented in the FIGURE which shows tumor volume versus post-implantation time for four sets of mice; a control, or untreated, set; a set receiving a dose of compound 1 of 10 mg/kg; a set receiving a dose of compound 1 of 20 mg/kg and a set receiving a dose of compound 1 of 30 mg/kg. As illustrated in the FIGURE, a significant dose-dependent inhibition of tumor growth was observed.

Equivalents

Those skilled in the art will recognize or be able to ascertain using no more than routine experimentation many equivalents to the specific embodiments of the invention described herein. Such equivalents are intended to be encompassed in the scope of the following claims.

We claim:

1. A compound of Formula I, $$A-B-NR^3-CHD-CH(OCH_3)-CH_2CO-E-K \quad (I),$$

wherein A is an amino acid residue of the formula $R^1R^2N-CHX-CO$, wherein $R^1$ is a methyl group or an ethyl group, $R^2$ is a hydrogen atom, a methyl group or an ethyl group, and X is a normal or branched $C_2-C_4$-alkyl group; B is an amino acid residue selected from the group consisting of valyl, isoleucyl, leucyl, and 2-$^t$butylglycyl; $R^3$ is a hydrogen atom or a methyl group; D is a normal or branched $C_2-C_5$-alkyl group; E is an amino acid residue selected from the group consisting of homoprolyl and 5-methylprolyl, or E is selected from the group consisting of

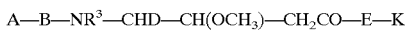

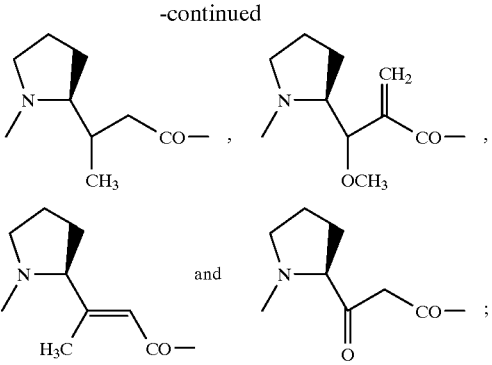

and K is an alkoxy group, a benzyloxy group or a substituted amino group; or a salt thereof with a pharmaceutically acceptable acid.

2. The compound of claim 1 wherein K is
   —N($C_{1-3}$-alkyl)$C_{1-3}$-alkyl, —NH—$C_{1-8}$-alkyl, —NH-($CH_3)_2$CN, —NH—C($CH_3)_2$CCH, —NH—C($CH_3)_2$ $CH_2CH_2OH$, —NH—C($CH_3)_2CH_2OH$, —NH—$C_{3-8}$-cycloalkyl, —NH-[3,3,0]-bicyclooctyl, —NHCH ($CH_3$) CH(OH) $C_6H_5$, —N($CH_3$) CH($CH_3$) CH(OH) $C_6H_5$, —NH-quinolyl, —NH-pyrazyl, —NH—$CH_2$-benzimidazolyl, —NH-adamantyl, —NH—$CH_2$-adamantyl, —NH—CH($CH_3$)-phenyl, —NH—C($CH_3$)

2-phenyl, —N(C$_{1-4}$-alkoxy)-C$_{1-4}$-alkyl, —N(C$_{1-4}$-alkoxy)—CH$_2$-phenyl, —N(C$_{1-4}$-alkoxy)phenyl, —N(CH$_3$)OBzl, —NH-(CH$_2$)$_v$-phenyl (v=0,1,2, or 3), which can be substituted by up to three substituents which can independently be CF$_3$, NO$_2$, methoxy, methyl, ethyl, N(CH$_3$)$_2$, halogen, or C$_{1-4}$-alkylsulfonyl, —NH-(CH$_2$)$_m$-naphthyl (m=0 or 1), —NH-(CH$_2$)$_w$-benzhydryl (w=0,1, or 2), —NH-biphenyl, —NH-pyridyl, —NH—CH$_2$-pyridyl, —NH—CH$_2$—CH$_2$-pyridyl, —NH-benzothiazolyl, —NH-benzoisothiazolyl, —NH-benzopyrazolyl, —NH-benzoxazolyl, —NH-(CH$_2$)$_m$-fluorenyl (m=0 or 1), —NH-pyrimidyl, —NH-(CH$_2$)$_m$-indanyl (m=0 or 1), —NH-(CH$_2$CH$_2$O)$_y$—CH$_3$ (y=0,1,2,3,4, or 5), —NH-(CH$_2$CH$_2$O)$_y$—CH$_2$CH$_3$ (y=0,1,2,3,4, or 5), —NH—NH—C$_6$H$_5$, —NH—NCH$_3$—C$_6$H$_5$, —NH—NH—CH$_2$-C$_6$H$_5$, and —NH—NCH$_3$—CH$_2$-C$_6$H$_5$; or K is selected from among the following:

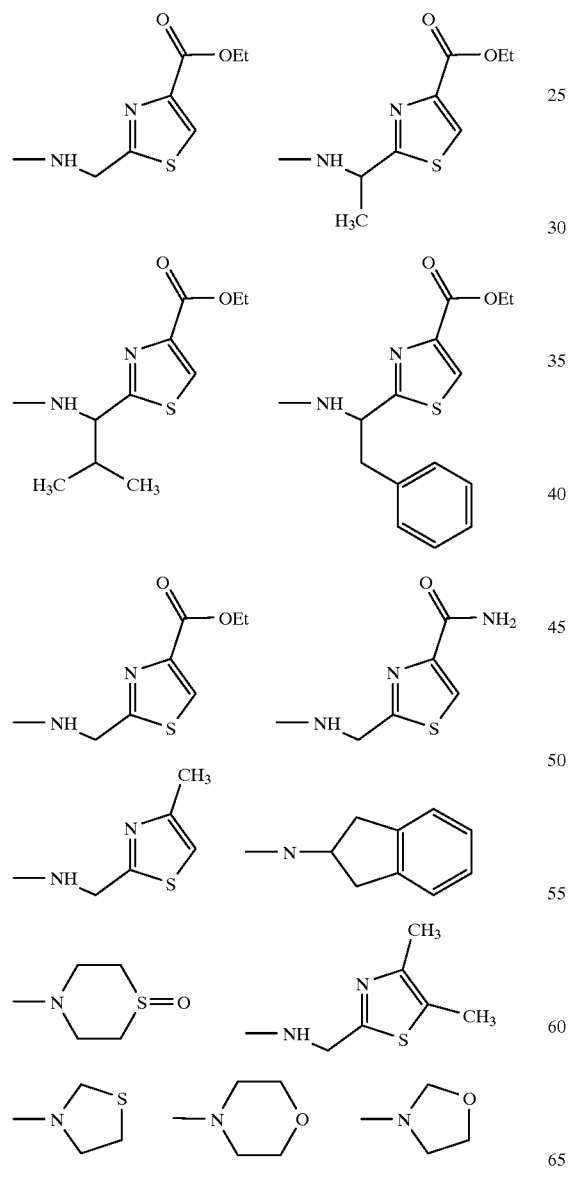

-continued

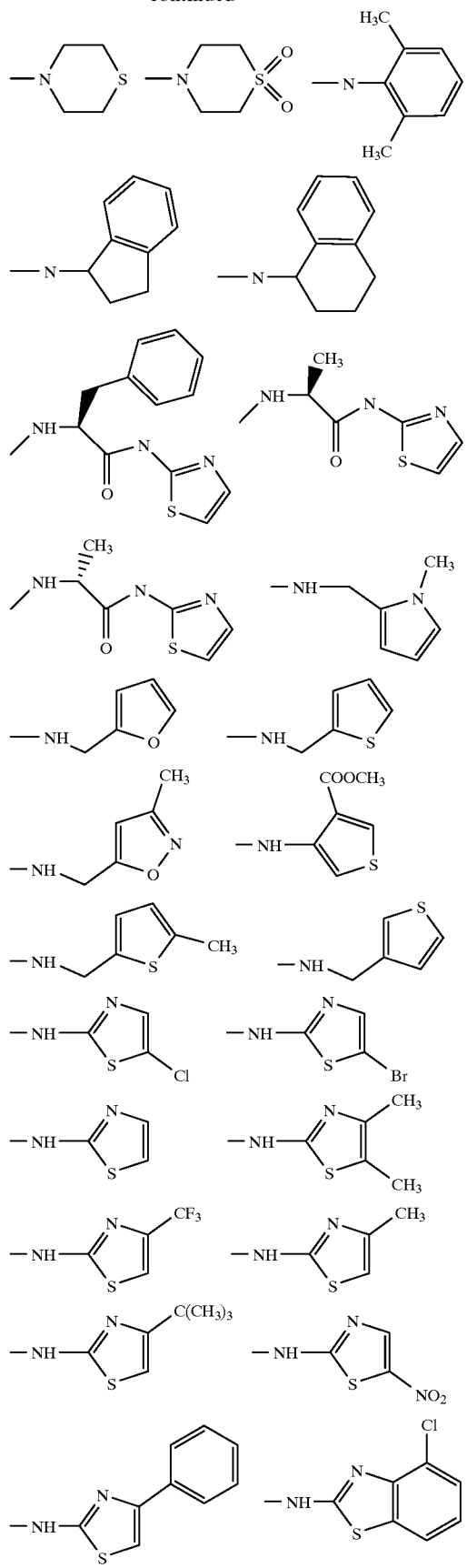

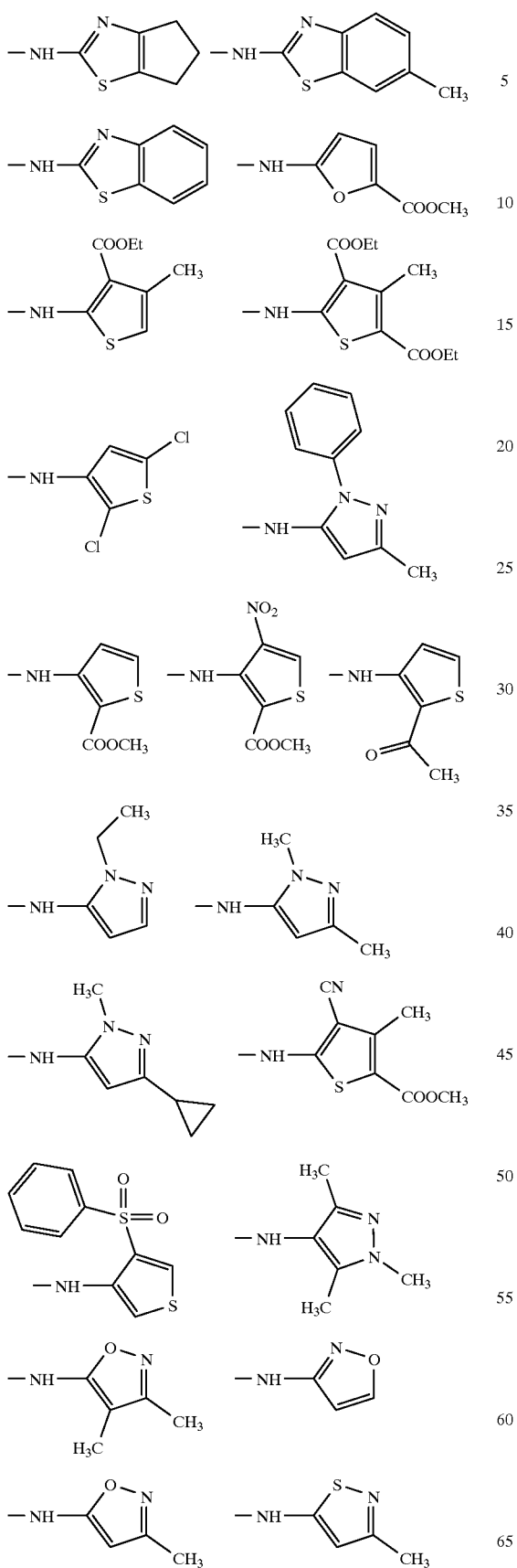
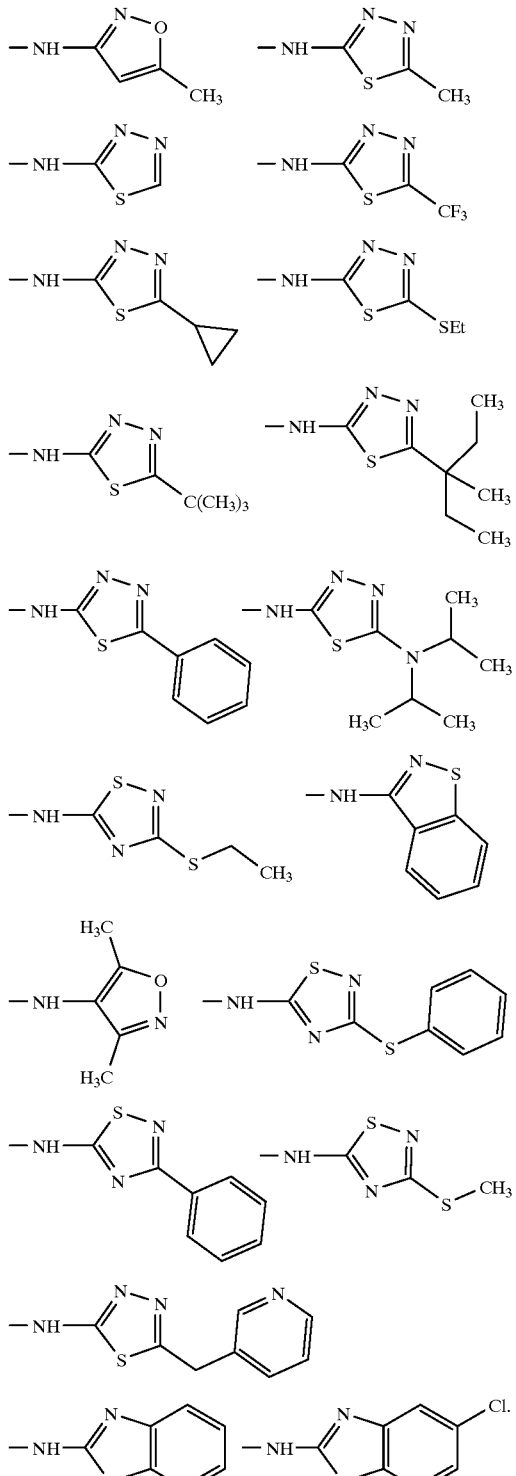

3. The compound of claim 1 wherein A is an amino acid residue of the formula $R^1R^2N$—CHX—CO, wherein $R^1$ is a methyl group, $R^2$ is a hydrogen atom or a methyl group, and X is an isopropyl, t-butyl or sec-butyl group; B is valyl, isoleucyl, or 2-t-butylglycyl; $R^3$ is a methyl group; D is an isopropyl, t-butyl or secbutyl group; E is a homoprolyl residue or E is selected from the group consisting of

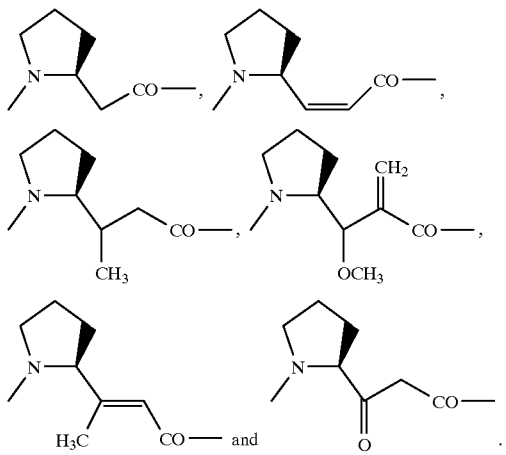

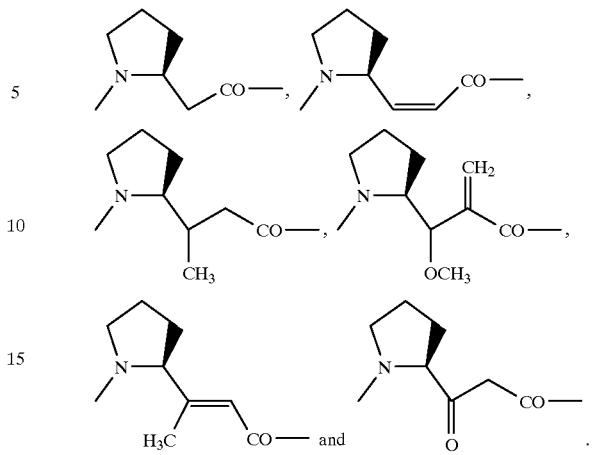

4. The compound of claim 3 wherein K is —OCH$_3$, —OC(CH$_3$)$_3$, —NHCH$_3$, —NHCH$_2$CH$_3$, —NH (CH$_2$)$_2$ CH$_3$, —NH(CH$_2$)$_3$CH$_3$, —NH(CH$_2$)$_4$CH$_3$, —NH(CH$_2$) CH$_3$, —NH(CH$_2$)$_6$CH$_3$, —NHCH(CH$_3$)$_2$, —NHCH (CH$_2$CH$_3$)$_2$, —NH(CH$_2$CH$_2$CH$_3$)$_2$, —NHC(CH$_3$)$_3$, —NH-cyclopropyl, —NH-cyclobutyl, —NH-cyclopentyl, —NH-cyclohexyl, —NH-cycloheptyl, —N[CH(CH$_3$)$_2$], CH(CH$_3$)$_2$, —N(CH$_3$)OCH$_3$, —N(CH$_3$)OCH$_2$CH$_3$, —N(CH$_3$) OCH$_2$CH$_2$CH$_3$, —N(CH$_3$) OCH(CH$_3$)$_2$, —N(CH$_2$CH$_3$)OCH$_3$, —N(CH$_2$CH$_3$) OCH$_2$CH$_3$, —N(CH$_3$) OCH$_2$C$_6$H$_5$, —N(OCH$_3$)CH$_2$-C$_6$H$_5$, —N(CH$_3$)OC$_6$H$_5$, —NH-phenyl, —NH-(3,4,5-trimethoxy)phenyl, —NH-(4-ethyl)phenyl, —NH—CH$_2$-C$_6$H$_5$, —NH(CH$_2$)$_2$C$_6$H$_5$, —NH (CH$_2$)$_3$C$_6$H$_5$, —NHCH(CH$_3$) CH(OH) C$_6$H$_5$, —N(CH$_3$) CH(CH$_3$)CH(OH)C$_6$H$_5$, —NH—CH$_2$-cyclohexyl, —NH-indanyl-(1), —NH—CH$_2$CF$_3$, —NHCH (CH$_2$F)$_2$, —NHC(CH$_3$)$_2$CH$_2$OH, —NH(CH$_2$CH$_2$O)$_2$ CH$_2$CH$_3$, —NHC(CH$_3$)$_2$CN, —NH-quinolyl, —NH-pyrazyl, —NH-adamantyl(2), —NH-adamantyl(1), —NH—CH$_2$-naphthyl, —NH-benzhydryl, —NH-biphenyl, —NH-pyridyl, —NH—CH$_2$-pyridyl, —NH—CH$_2$-CH$_2$-pyridyl, —NH-benzothiazolyl, —NH-benzoisothiazolyl, —NH-benzopyrazolyl, —NH-benzoxazolyl, —NH-fluorenyl, —NH-pyrimidyl, —NH—CH$_2$-(4-methyl)-thiazolyl(2), —NH—CH$_2$-furanyl(2), —NH—CH$_2$-thienyl (2), —NH—CH$_2$-(5-methyl)thienyl(2), —NH-thiazolyl(2), —NH-isoxazolyl(3), —NH-(3-methyl)isoxazolyl(5), —NH-(3-methyl)isothiazolyl(5), —NH-(5-trifluoromethyl)-thiadiazolyl (2), —NH-(5-cyclopropyl)thiadiazolyl(2), —NH-(4,5-dimethyl)thiazolyl(2), —NH-(5-methyl)-thiadiazolyl(2), -Phe-thiazolyl (2) amide, -L-Ala-thiazolyl (2) amide, -D-Ala-thiazolyl(2)amide, or K is selected from among the following:

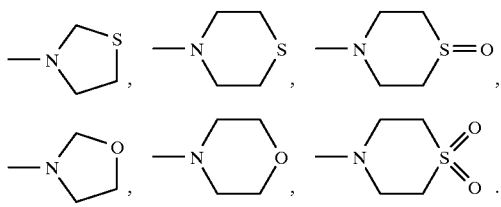

5. The compound of claim 1 wherein A is N,N-dimethylvalyl B is valyl; R$^3$ is methyl; D is an isopropyl or sec-butyl group; E is selected from the group consisting of 5-methylprolyl and homoprolyl or E is selected from the group consisting of 6. The compound of claim 5 wherein K is —OCH$_3$, —OCH$_2$CH$_3$, —NHCH$_3$, —NHCH$_2$CH$_2$CH$_3$, —N[(CH (CH$_3$)$_2$]$_2$, —NH-phenyl, —N(CH$_3$) (CH$_2$C$_6$H$_5$), —NH-(3,4,5-trimethoxy)phenyl, —NH-(4-ethyl) phenyl, —NH—CH$_2$-C$_6$H$_5$, —NH (CH$_2$)$_2$C$_6$H$_5$, —NHCH(CH$_3$)CH(OH) C$_6$H$_5$, —N(CH$_3$) CH(CH$_3$) CH(OH) C$_6$H$_5$, —NH-pyridyl, —NH—CH$_2$—CH$_2$-pyridyl, —NH-benzothiazolyl, —NH-thiazolyl(2), —NH-(4,5-dimethyl)thiazolyl(2), —NH-(5-methyl)-thiadiazolyl(2), -phenylalanyl-thiazolyl(2)amide, -L-alanyl-thiazolyl(2)amide or -D-alanyl-thiazolyl(2)amide.

7. The compound of claim 5 wherein A is N,N-dimethylvalyl, R$^3$ is a methyl group, D is an isopropyl or sec-butyl group and B is valyl.

8. The compound of claim 7 wherein K is selected from the group consisting of —NHCH$_3$, —NHCH$_2$CH$_2$CH$_3$, —N [(CH(CH$_3$)$_2$]$_2$, —NH-phenyl, —N(CH$_3$) (CH$_2$C$_6$H$_5$), —NH-(3,4,5-trimethoxy)phenyl, —NH-(4-ethyl)phenyl, —NH—CH$_2$-C$_6$H$_5$, —NH (CH$_2$)$_2$C$_6$H$_5$, —NHCH(CH$_3$) CH(OH) C$_6$Hs, —N(CH$_3$) CH(CH$_3$) CH(OH) C$_6$H$_5$, —NH-pyridyl, —NH—CH$_2$-CH$_2$-pyridyl, —NH-benzothiazolyl, —NH-thiazolyl(2), —NH-(4,5-dimethyl)thiazolyl(2), —NH-(5-methyl)-thiadiazolyl(2), -Phe-thiazolyl(2)amide, -L-Ala-thiazolyl(2)amide, and -D-Ala-thiazolyl(2)amide.

9. A pharmaceutical composition comprising a y pharmaceutically acceptable carrier and a therapeutically effective amount of a compound of claim 1.

10. A method for treating a tumor in a mammal, comprising administering to the mammal a tumor-inhibiting amount of a compound of claim 1.

11. The method of claim 10 wherein the tumor is a colon tumor, a breast tumor or a lung tumor.

12. A compound of Formula I, $$A—B—NR^3—CHD—CH(OCH_3)—CH_2CO—E—K \qquad (I),$$

wherein A is an amino acid residue selected from the group consisting of N-methyl-D-prolyl, N-methyl-D-homoprolyl and N,N-dimethyl-2-ethyl-2-phenylglycyl; B is an amino acid residue selected from the group consisting of valyl, isoleucyl, leucyl, and 2-$^t$butylglycyl; R$^3$ is a hydrogen atom or a methyl group; D is a normal or branched C$_2$–C$_5$alkyl group; E is an amino acid residue selected from the group consisting of prolyl, homoprolyl, 5-methylprolyl, and phenylalanyl, or E is

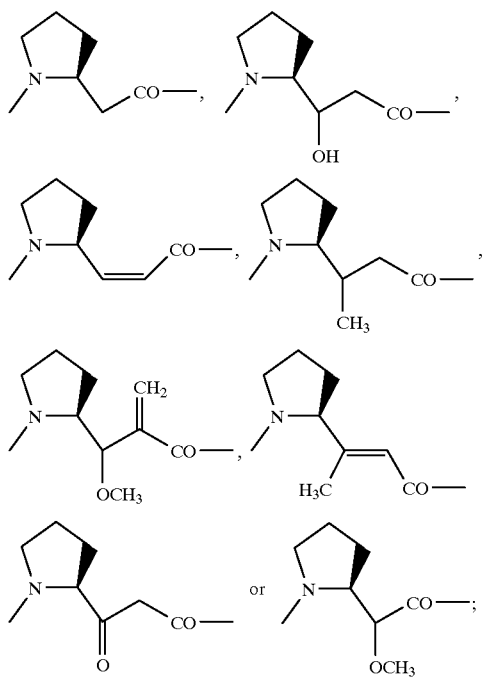

and K is an alkoxy group, a benzyloxy group or a substituted amino group; or a salt thereof with a pharmaceutically acceptable acid.

13. The compound of claim 12 wherein K is —N($C_{1-3}$-alkyl)$C_{1-3}$-alkyl, —NH—$C_{1-8}$-alkyl, —NH—C(CH$_3$)$_2$CN, —NH—C(CH$_3$)$_2$CCH, —NH—C(CH$_3$)$_2$CH$_2$CH$_2$OH, —NH—C(CH$_3$)$_2$CH$_2$OH, —NH—$C_{3-8}$-cycloalkyl, —NH-[3,3,0]-bicyclooctyl, —NHCH(CH$_3$)CH(OH)C$_6$H$_5$, —N(CH$_3$)CH(CH$_3$)CH(OH)C$_6$H$_5$, —NH-quinolyl, —NH-pyrazyl, —NH—CH$_2$-benzimidazolyl, —NH-adamantyl, —NH—CH$_2$-adamantyl, —NH—CH(CH$_3$)-phenyl, —NH—C(CH$_3$)$_2$-phenyl, —N($C_{14}$-alkoxy)-$C_{1-4}$-alkyl, —N($C_{14}$-alkoxy)—CH$_2$-phenyl, —N($C_{1-4}$-alkoxy)phenyl, —N(CH$_3$)OBzl, —NH-(CH$_2$)$_v$-phenyl (v=0,1,2, or 3), which can be substituted by up to three substituents which can independently be CF$_3$, NO$_2$, methoxy, methyl, ethyl, N(CH$_3$)$_2$, halogen, or $C_{1-4}$-alkylsulfonyl, —NH-(CH$_2$)-naphthyl (m=0 or 1), —NH-(CH$_2$)$_w$-benzhydryl (w=0,1, or 2), —NH-biphenyl, —NH-pyridyl, —NH—CH$_2$-pyridyl, —NH—CH$_2$-CH$_2$-pyridyl, —NH-benzothiazolyl, —NH-benzoisothiazolyl, —NH-benzopyrazolyl, —NH-benzoxazolyl, —NH-(CH$_2$)$_m$-fluorenyl (m=0 or 1), —NH-pyrimidyl, —NH-(CH$_2$)$_m$-indanyl (m=0 or 1), —NH-(CH$_2$CH$_2$O)$_y$—CH$_3$ (y=0,1,2,3,4, or 5), —NH-(CH$_2$CH$_2$O)$_y$—CH$_2$CH$_3$ (y=0,1,2,3,4, or 5), —NH—NH—C$_6$H$_5$, —NH—NCH$_3$—C$_6$H$_5$, —NH—NH—CH$_2$-C$_6$H$_5$, and —NH—NCH$_3$—CH$_2$-C$_6$H$_5$; or K is selected from among the following:

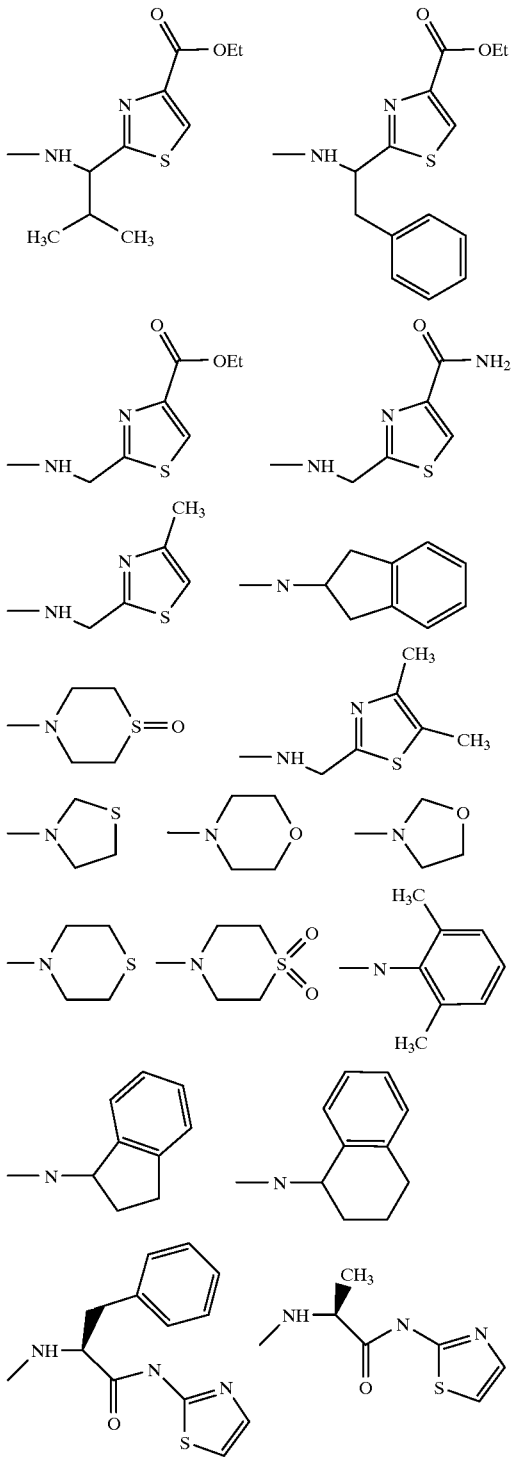

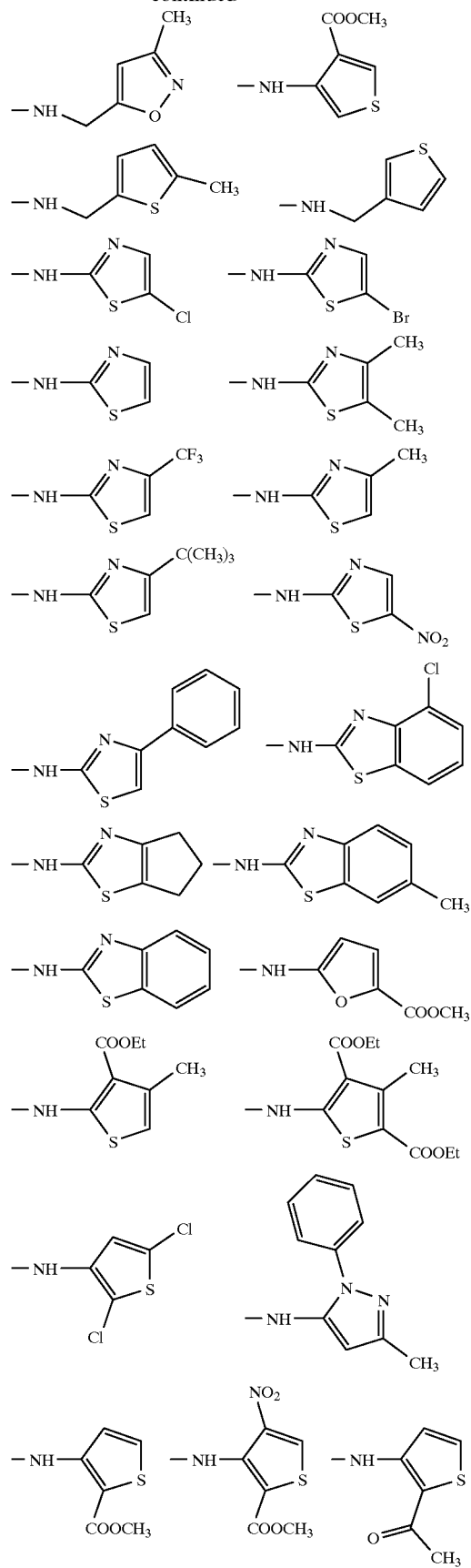
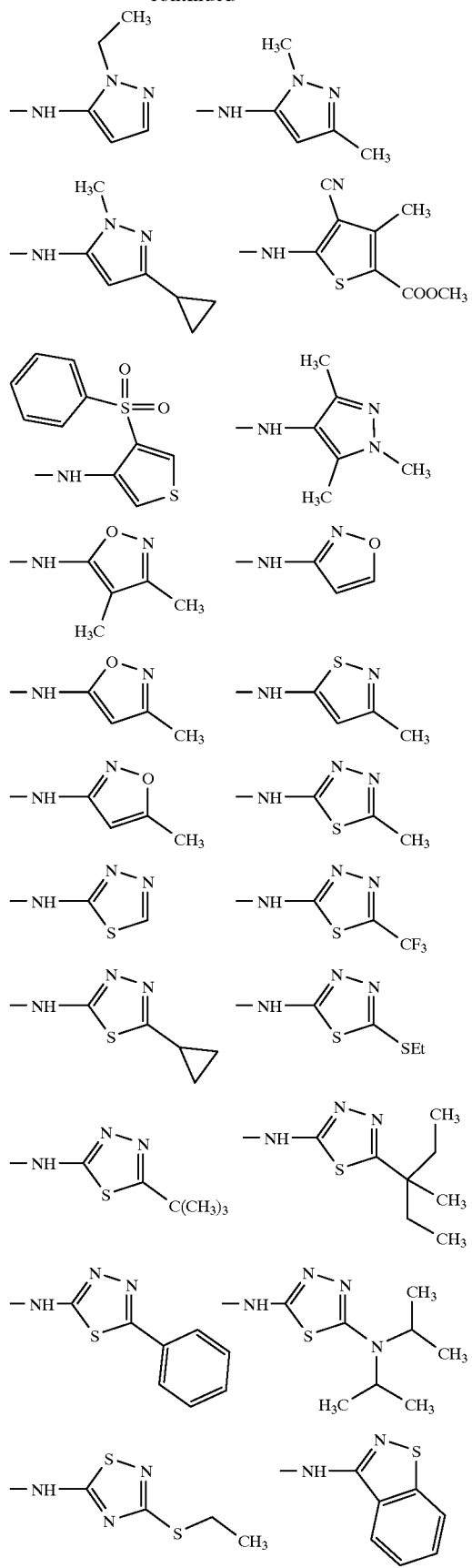

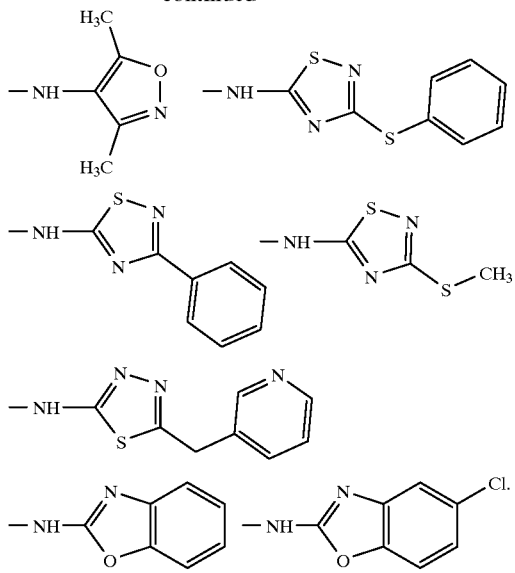

14. The compound of claim 12 wherein B is valyl; $R^3$ is methyl; D is an isopropyl or sec-butyl group; and E is a prolyl or homoprolyl residue or E is

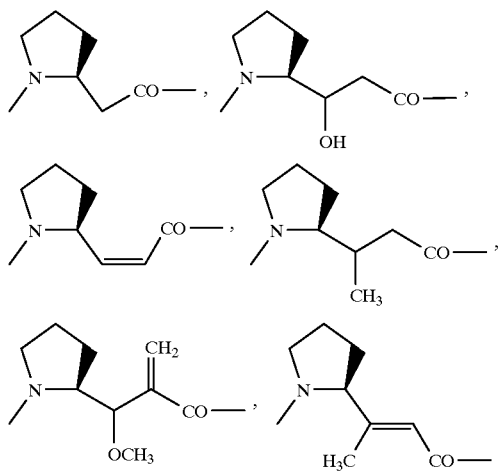

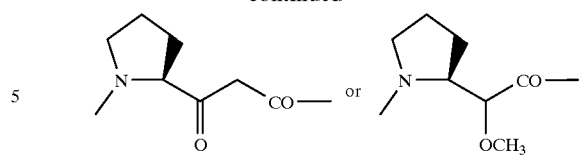

15. The compound of claim 14 wherein K is —OCH₃, —OC(CH₃)₃, —NHCH₃, —NHCH₂CH₃, —NH(CH₂)₂CH₃, —NH(CH₂)₃CH₃, —NH(CH₂)₄CH₃, —NH(CH₂)₅CH₃, —NH(CH₂)₆CH₃, —NHCH(CH₃)₂, —NHCH(CH₂CH₃)₂, —NH(CH₂CH₂CH₃)₂, —NHC(CH₃)₃, —NH-cyclopropyl, —NH-cyclobutyl, —NH-cyclopentyl, —NH-cyclohexyl, —NH-cycloheptyl, —N[CH(CH₃)₂]CH(CH₃)₂, —N(CH₃)OCH₃, —N(CH₃)OCH₂CH₃, —N(CH₃)OCH₂CH₂CH₃, —N(CH₃)OCH(CH₃)₂, —N(CH₂CH₃)OCH₃, —N(CH₂CH₃)OCH₂CH₃, —N(CH₃)OCH₂C₆H₅, —N(OCH₃)CH₂—C₆H₅, —N(CH₃)OC₆H₅, —NH-phenyl, —NH-(3,4,5-trimethoxy)phenyl, —NH-(4-ethyl)phenyl, —NH—CH₂—C₆H₅, —NH(CH₂)₂C₆H5, —NH(CH₂)₃C₆H₅, —NHCH(CH₃) CH(OH) C₆H₅, —N(CH₃) CH(CH₃) CH(OH) C₆H₅, —NH—CH₂-cyclohexyl, —NH-indanyl-(1), —NH—CH₂CF₃, —NHCH(CH₂F)₂, —NHC(CH₃)₂CH₂OH, —NH (CH₂CH₂O)₂CH₂CH₃, —NHC(CH₃)₂CN, —NH-quinolyl, —NH-pyrazyl, —NH-adamantyl(2), —NH-adamantyl(1), —NH—CH₂-naphthyl, —NH-benzhydryl, —NH-biphenyl, —NH-pyridyl, —NH—CH₂-pyridyl, —NH—CH₂—CH₂-pyridyl, —NH-benzothiazolyl, —NH-benzoisothiazolyl, —NH-benzopyrazolyl, —NH-benzoxazolyl, —NH-fluorenyl, —NH-pyrimidyl, —NH—CH₂-(4-methyl)-thiazolyl(2), —NH—CH₂-furanyl(2), —NH—CH₂-thienyl(2), —NH—CH₂-(5-methyl)thienyl(2), —NH-thiazolyl(2), —NH-isoxazolyl(3), —NH-(3-methyl)isoxazolyl(5), —NH-(3-methyl)isothiazolyl(5), —NH-(5-trifluoromethyl)-thiadiazolyl(2), —NH-(5-cyclopropyl)thiadiazolyl(2), —NH-(4,5-dimethyl)thiazolyl(2), —NH-(5-methyl)-thiadiazolyl(2), -Phe-thiazolyl(2)amide, -L-Ala-thiazolyl(2)amide, -D-Ala-thiazolyl(2)amide, or K is selected from among the following:

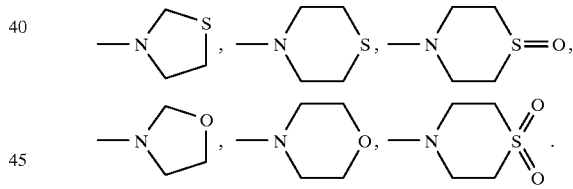

* * * * *